United States Patent [19]
Chin

[11] Patent Number: 5,769,850
[45] Date of Patent: Jun. 23, 1998

[54] APPARATUS AND METHOD FOR SUBMERGIBLE, SELF-RETAINING DISTRACTION OSTEOGENESIS

[76] Inventor: Martin Chin, 20 Hampton Ct., Alameda, Calif. 94502

[21] Appl. No.: 732,064

[22] Filed: Oct. 16, 1996

[51] Int. Cl.$^6$ .................................................. A61B 17/56
[52] U.S. Cl. .............................. 606/53; 606/60; 606/69; 606/71; 606/105; 606/102; 606/73
[58] Field of Search ................................. 606/53, 60, 69, 606/70, 71

[56] References Cited

U.S. PATENT DOCUMENTS

| | | | |
|---|---|---|---|
| 4,439,152 | 3/1984 | Small | 433/173 |
| 4,573,917 | 3/1986 | Erickson | 433/75 |
| 4,615,338 | 10/1986 | Ilizarov et al. | 128/92 A |
| 4,616,633 | 10/1986 | Vargas Garcia | 128/20 |
| 4,616,634 | 10/1986 | Vargas Garcia | 128/20 |
| 4,778,471 | 10/1988 | Bajpai | 623/16 |
| 4,813,869 | 3/1989 | Gatewood | 433/18 |
| 4,890,631 | 1/1990 | Hardy | 606/59 |
| 4,988,358 | 1/1991 | Eppley et al. | 623/16 |
| 5,020,536 | 6/1991 | Keen | 128/402 |
| 5,092,883 | 3/1992 | Eppley et al. | 623/11 |
| 5,205,746 | 4/1993 | Chanavaz | 433/174 |
| 5,211,664 | 5/1993 | Tepic et al. | 623/16 |
| 5,218,035 | 6/1993 | Liu | 524/414 |
| 5,224,958 | 7/1993 | Warunek et al. | 623/11 |
| 5,262,166 | 11/1993 | Liu et al. | 424/423 |
| 5,275,598 | 1/1994 | Cook | 606/54 |
| 5,281,265 | 1/1994 | Liu | 106/35 |
| 5,350,382 | 9/1994 | Armstrong | 606/87 |
| 5,361,506 | 11/1994 | Beeuwkes, III | 33/512 |
| 5,364,396 | 11/1994 | Robinson et al. | 606/53 |
| 5,380,328 | 1/1995 | Morgan | 606/70 |
| 5,389,323 | 2/1995 | Cook | 264/136 |
| 5,437,668 | 8/1995 | Aronson et al. | 606/57 |
| 5,474,063 | 12/1995 | Riendeau | 128/207.18 |

OTHER PUBLICATIONS

Akizuki, T., et al., "Mid–face Distraction," Craniofacial Surgery–Proceedings of the Sixth International Congress of The International Society of Cranio–Facial Surgery, Saint–Tropez 1995.

Chin, M., et al., "Distraction Osteogenesis in Craniofacial Surgery Using Internal Devices," Craniofacial Surgery–Proceedings of the Sixth International Congress of The International Society of Cranio–Facial Surgery, Saint–Tropez 1995.

(List continued on next page.)

Primary Examiner—Michael Buiz
Assistant Examiner—David O. Reip
Attorney, Agent, or Firm—Fliesler, Dubb, Meyer & Lovejoy LLP

[57] ABSTRACT

An apparatus and method for submergible self-retaining distraction osteogenesis is provided. Distraction osteogenesis devices are submerged below a layer of tissue and/or skin layers and are activated based upon maximum pressures, rather than constant activation rates. Distraction osteogenesis devices are also self-retaining in that the force in displacing bone segments is transferred substantially through metal plates, rather than screws or fixation points. In particular, zygomatic, alveolar and mandibular distraction osteogenesis devices are provided. The zygomatic and alveolar distraction osteogenesis devices include a submergible first and second metal plate along with a threaded rod. The zygomatic and alveolar distraction osteogenesis devices are activated using a cannula, torque wrench adapter and torque wrench. The mandibular distraction osteogenesis device includes a palate expander having a plurality of rods used in coupling first and second self-retaining U-shaped plates. The mandibular distraction osteogenesis device is activated using an alien wrench. In order to allow for maximum bone growth and/or distraction, a maximum pressure between bone segments is applied by a torque or allen wrench.

5 Claims, 17 Drawing Sheets

OTHER PUBLICATIONS

Chin, Martin, DDS, et al. "Distraction Osteogenesis in Maxillofacial Surgery Using Internal Devices: Review of Five Cases," Journal of Oral and Maxillofacial Surgeons, vol. 54, pp. 45–53, 1996.

Costantino, Maj Peter D., MC, USAF; et al., "Experimental Mandibular Regrowth by Distraction Osteogenesis–Long-term Results," Arch Otolaryngol Head Neck Surg—vol. 119, May 1993.

Diner, P.A., et al., "Intraoral Distraction for Mandibular Lengthening," Craniofacial Surgery–Proceedings of the Sixth International Congress of The International Society of Cranio–Facial Surgery, Saint–Tropez 1995.

Fairley, J., et al., "Continuous Midfacial Distraction," Craniofacial Surgery–Proceedings of the Sixth International Congress of The International Society of Cranio–Facial Surgery, Saint–Tropez 1995.

Guerrero,, R., et al., "Craniofacial Osteogenesis by Gradual Distraction" Craniofacial Surgery–Proceedings of the Sixth International Congress of The International Society of Cranio–Facial Surgery, Saint–Tropez 1995.

McCormick, Suzanne, DDS, "Distraction Osteogenesis," Dentistry Today, Sep. 1996, p. 58.

Monasterio, F. O., et al., "Simultaneous Mandibular and Maxillary Distraction," Craniofacial Surgery–Proceedings of the Sixth International Congress of The International Society of Cranio–Facial Surgery, Saint–Tropez 1995.

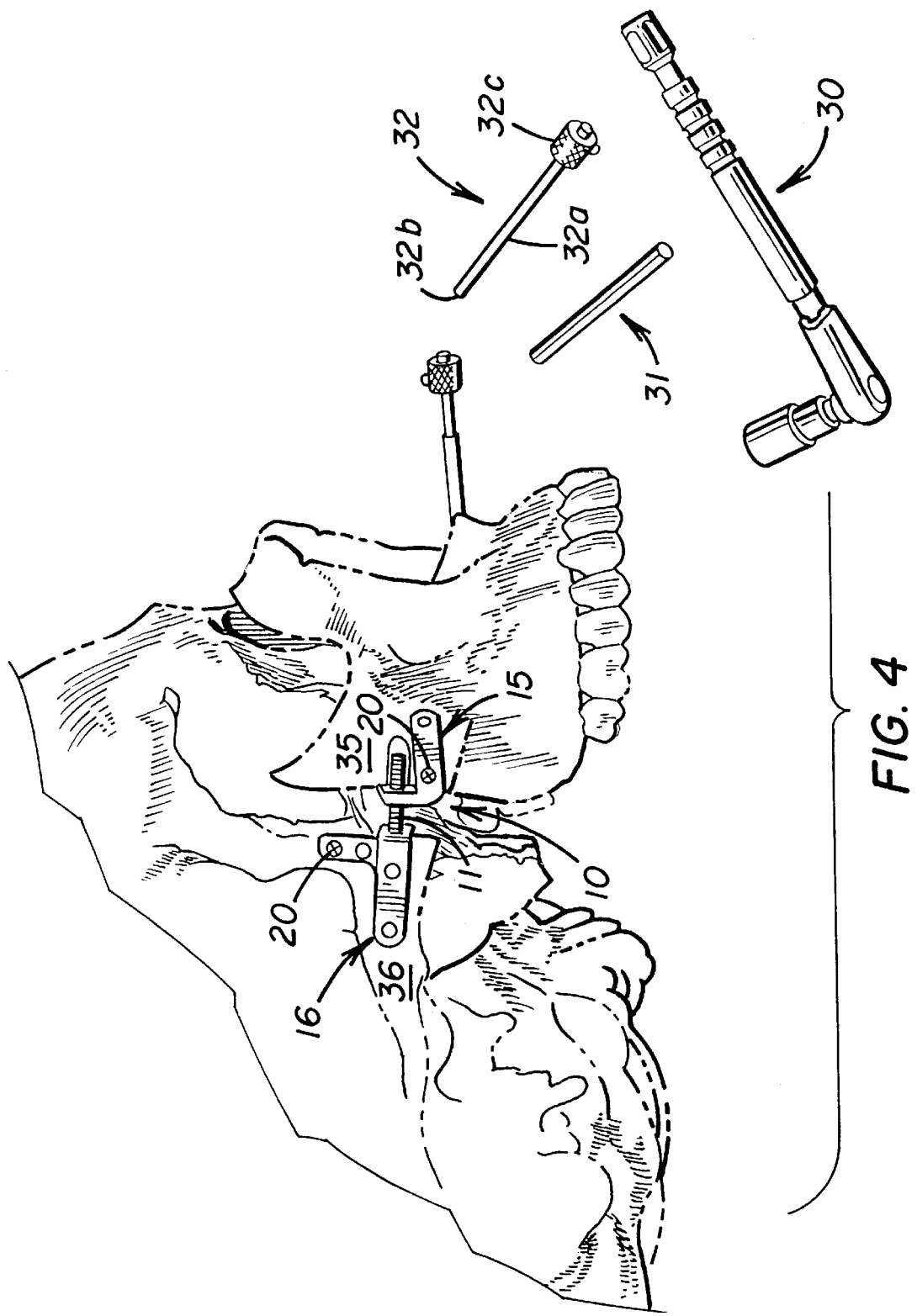

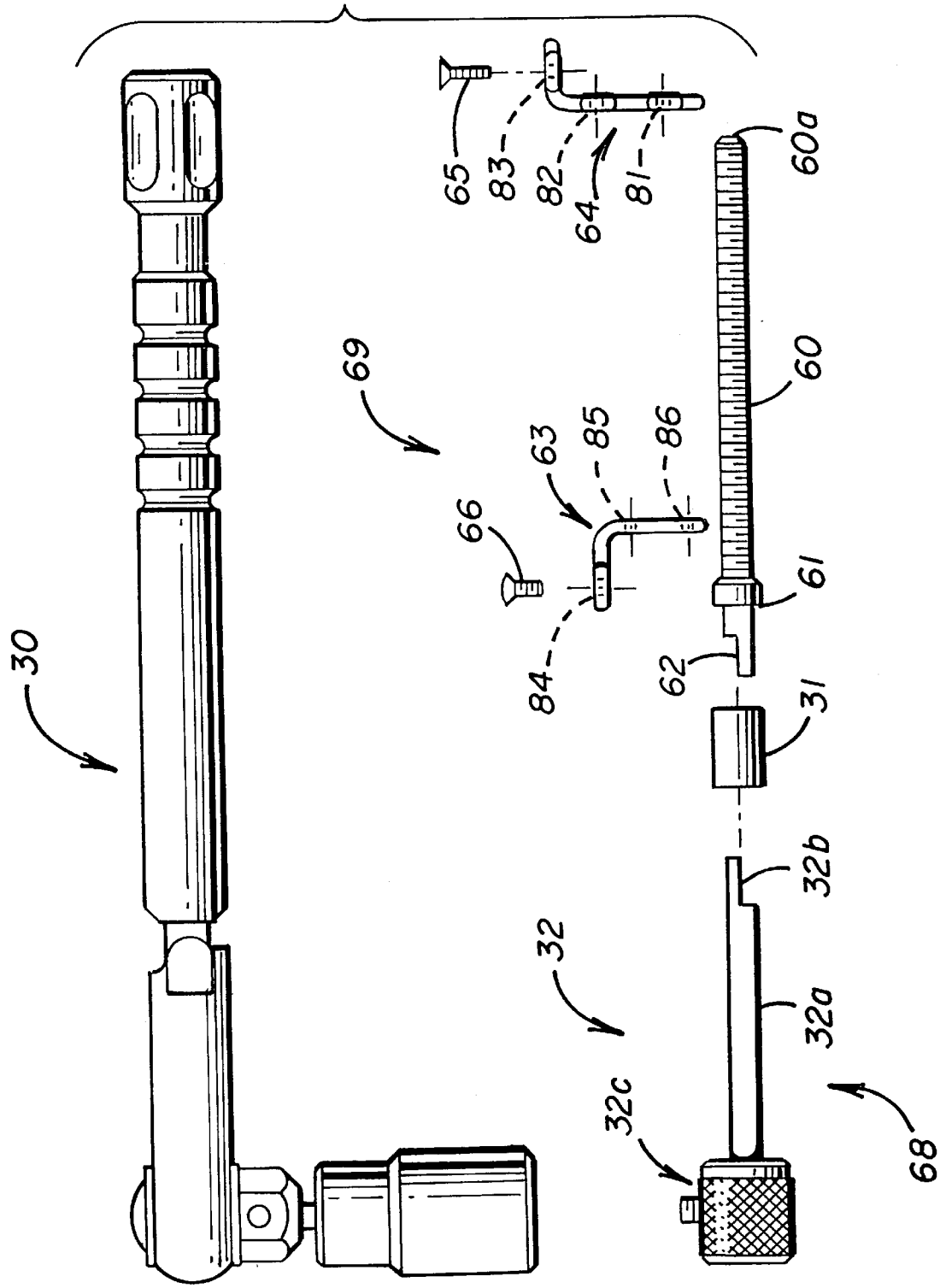

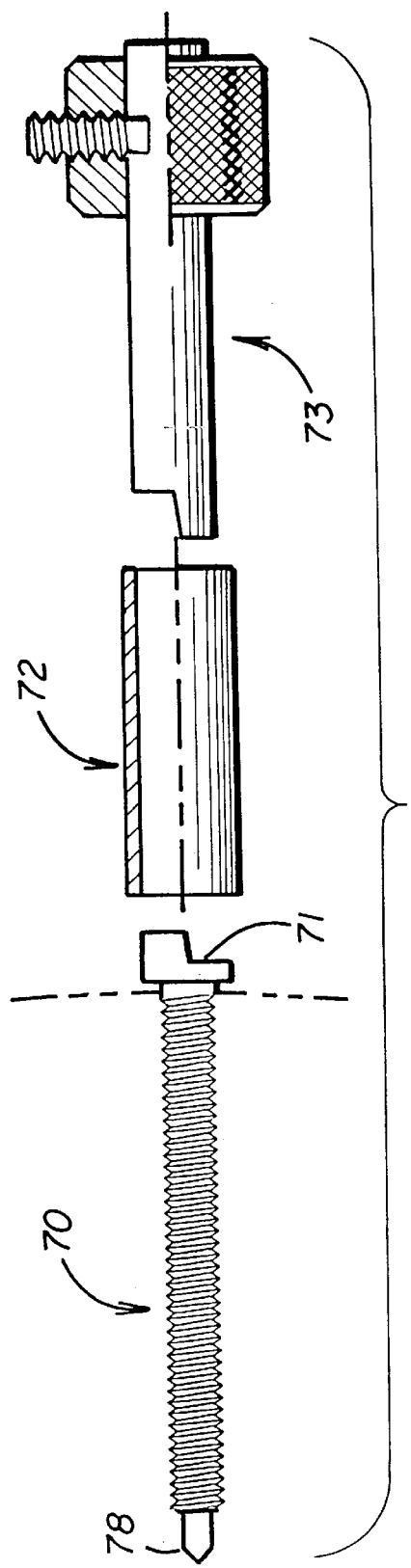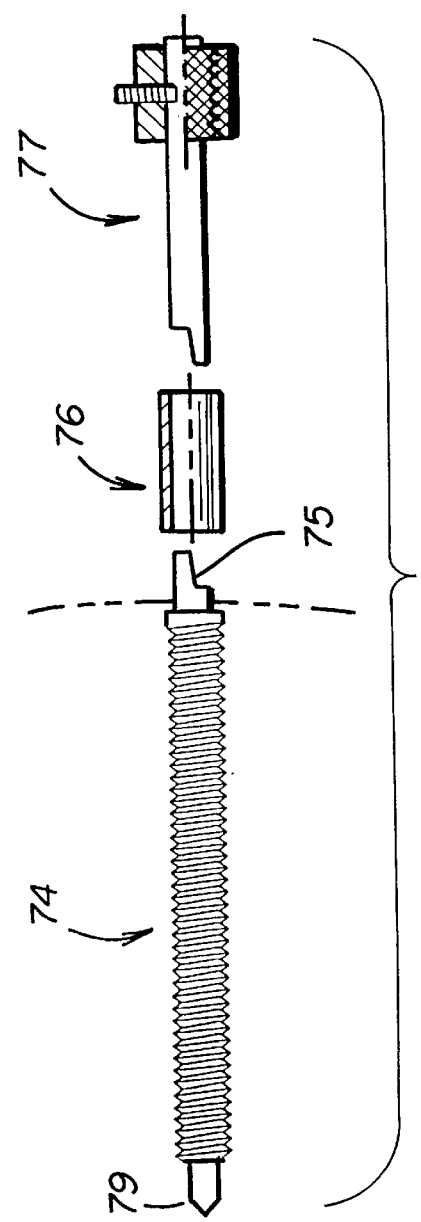
FIG. 11a
FIG. 11b

APPARATUS AND METHOD FOR SUBMERGIBLE, SELF-RETAINING DISTRACTION OSTEOGENESIS

BACKGROUND OF THE INVENTION

1. Field of the Invention

The present invention relates to distraction osteogenesis.

2. Description of the Related Art

Distraction osteogenesis refers to a technique for growing bone or osteogenesis material, as well as soft tissue, by separating two bone segments. Generally, an osteotomy, such as a Lefort III osteotomy, is performed which partitions a bone into two bone segments. External distraction osteogenesis devices are then attached to the bone segments through soft tissue or a skin layer. These external distraction osteogenesis devices may include rods and rings or other cumbersome metal components. The distraction osteogenesis devices form a gap between the bone segments by exerting pressure between the bone segments. As the gap between the bone segments widens, the body's own natural healing capacity fills the void with new bone and adjacent soft tissue. Once the desired bone formation is achieved, the area is allowed to heal and consolidate. Often, the distraction osteogenesis device is then removed.

An example of a distraction osteogenesis device is an Ilizarov distractor. Typically, an Ilizarov distractor is used in lengthening individuals' limbs, such as a leg. In this application, an Ilizarov distractor may include external metal rings which are then secured to two bone segments in a leg. These metal rings are then attached by a rod assembly which may be used to form a gap between the two bone segments and thus allow for the formation of new bone. A description of an Ilizarov distractor may be found in U.S. Pat. No. 4,615,338, issued to Ilizarov, et al. on Oct. 7, 1986 and entitled "Automatic Compression - Distraction Apparatus."

Distraction osteogenesis devices may also be used in growing bone in the craniofacial region of small children. Often, distraction osteogenesis devices are used on small children who are missing bone due to birth abnormalities or accidents. While distraction osteogenesis devices are often used on children, distraction osteogenesis devices may be used on adults and animals as well.

A number of problems are encountered in using present distraction osteogenesis devices. First, distraction osteogenesis devices are generally external, which may cause a number of problems or complications. Often, cumbersome metal rods and rings located external to an individual's skin are used to distract or separate bone segments. Individuals, and in particular small children, may fall and injure themselves on the protruding metal edges. Further, small children may complicate the distraction osteogenesis procedure by improperly adjusting the osteogenesis distraction device.

The distraction osteogenesis device may require multiple entry points to an individual's skin and thus may create multiple scars. Distraction osteogenesis devices requiring multiple entry points may also increase the likelihood of infection due to the multiple openings in the individual's skin. Also, individuals undergoing the distraction osteogenesis procedure have to cope with an external device which is not cosmetically appealing.

A second problem encountered with distraction osteogenesis devices regards customizing devices for individuals. Generally, a distraction osteogenesis device used for one individual would not be suitable for another. In distraction osteogenesis devices used in the craniofacial area, distraction osteogenesis devices must be measured to fit specific surface areas of craniofacial bones. Also, individuals may have different amounts of bone caused by different types of birth abnormalities or accidents, thus requiring customized distraction osteogenesis devices due to limited bone.

Third, distraction osteogenesis devices are attached to bone segments in such a way that the point of fixation to the bone transfers force during activation. For example, a distraction osteogenesis device may be attached to a bone segment by a bone screw or rod which transfers a substantial amount of force during activation or when the distraction osteogenesis device is exerting pressure between the bone segments. By having the bone screw transfer a substantial amount of the force during activation, the distraction osteogenesis device may be dislodged from the bone.

Fourth, distraction osteogenesis devices are activated using constant rates which do not reflect the individual's healing abilities. Regardless of the age or condition of the individual, distraction osteogenesis devices are activated by widening the gap between bone segments 0.25–0.50 mm four times per day. This conventional activation rate results in bone growth as low as 20 mm in 20 days. Accordingly, an individual may have to be under constant medical supervision for up to 20 days. An individual could be an outpatient, but would need to return to the hospital four times per day for adjustments. Present distraction osteogenesis device activation techniques do not take into account an individual's ability to grow bone at a greater or lesser rate. By using this constant rate, bone may grow too quickly and lock the distraction osteogenesis device, or in the alternative, bone may grow too slowly, requiring a longer period of time that the distraction osteogenesis device is necessary.

Therefore, it is desirable to provide a distraction osteogenesis device which is submergible, or beneath an individual's skin or soft tissue. The distraction osteogenesis device then could be permanently positioned within an individual, thereby eliminating the need for surgery in removing the device, including the associated risks and costs. The distraction osteogenesis device then would be more cosmetically appealing and reduce the likelihood of infection, injury and/or scaring. Further, it is desirable to have a distraction osteogenesis device which does not have to be customized for each individual. Manufacturing and medical costs would then be substantially reduced by using a standard distraction osteogenesis device and method, rather than customizing distraction osteogenesis devices and methods for each individual. The distraction osteogenesis device also should be affixed to bone in such a way that a substantial amount of the force used in activation is not transferred through a fastening device (i.e., screw, pin or rod). Finally, the distraction osteogenesis device should be activated at a rate which optimizes bone growth.

SUMMARY OF THE INVENTION

According to an aspect of the present invention, an apparatus is provided for distracting a first bone segment from a second bone segment. The apparatus comprises a first implantable plate for coupling the first bone segment and a second implantable plate for coupling the second bone segment. Submergible means is coupled to the first plate and the second plate which positions the first plate a distance from the second plate responsive to a force.

According to another aspect of the present invention, the submergible means includes a threaded rod portion.

According to another aspect of the present invention, the submergible means includes a palate expander having a plurality of rods.

According to another aspect of the present invention, the apparatus includes activating means for transferring a force to the submergible means.

According to another aspect of the present invention, the activating means includes a cannula, a torque wrench adapter and a torque wrench.

According to another aspect of the present invention, the apparatus includes means for removing the activating means.

According to another aspect of the present invention, the first and second plates transfer a substantial amount of the force.

According to another aspect of the present invention, the activating means transfers a force generating a maximum pressure in order to achieve a maximum distance.

According to another aspect of the present invention, a submergible device for distracting a first segment of the zygoma from a second segment of the zygoma to allow for bone generation is provided.

The submergible device includes an implantable rod having a threaded portion, a base and an activation end. An implantable L-shaped member is coupled to the first segment of the zygoma and has a protruding portion for inserting the threaded portion of the rod. An implantable curved metal member is coupled to the second segment of the zygoma and has an opening for positioning the rod activation end. The rod base transfers a force against the curved member, creating a distance between the first and second zygoma segments responsive to a force.

According to another aspect of the present invention, a method for forming zygomatic bone is provided. The method includes the steps of (a) cutting the zygoma into first and second segments; (b) forming a first notch in a first segment; (c) forming a first notch in a second segment; (d) securing a first plate under a layer of tissue to the notch in the first segment; (e) coupling a rod to the first plate; (f) securing a second plate under the layer of tissue to the notch in the second segment; and (g) exerting a force on the rod in order to displace the first segment of zygoma from the second segment of zygoma.

According to another aspect of the present invention, a submergible device for distracting a first segment of alveolus from a second segment of alveolus to allow for bone generation is provided. The submergible device comprises a rod having a threaded portion, including an end, a base and an activation end. A first member is coupled to the first segment of alveolus and has an opening for inserting the rod end. A second member is coupled to the second segment of alveolus and has an opening for positioning the threaded portion of the rod. The rod transfers a force against the second member, creating a distance between the first and second alveolus segments.

According to another aspect of the present invention, a method for forming alveolar bone is provided. The method includes the steps of:

(a) cutting the alveolus into first and second segments; (b) securing a first plate to the first segment of alveolus; (c) forming an opening in the second segment of alveolus; (d) securing a second transport plate to the second segment of alveolus; (e) inserting a rod into the opening of the second segment of alveolus and through the second plate opening to the first plate; and (f) exerting a force on the rod to displace the first segment of alveolus from the second segment of alveolus.

According to another aspect of the present invention, a submergible device for distracting a first segment of mandible from a second segment of mandible to allow for bone generation is also provided. The submergible device comprises a first U-shaped member which is coupled to the first segment of mandible. A second U-shaped metal member is coupled to a second segment of mandible. A palate expander having a first pair of rods and second pair of rods is coupled to the first U-shaped member and the second U-shaped member, respectively. The palate expander transfers a force against the first and second U-shaped members, creating a distance between the first and second mandible segments.

According to another aspect of the present invention, a method for forming mandibular bone is provided. The method comprises the steps of: (a) cutting the mandible into first and second segments; (b) coupling a first member to a palate expander; (c) coupling a second member to the palate expander; (d) positioning the palate expander between the first and second segment; (e) securing the first and second members to the first and second segments of mandible; and (f) activating the palate expander in order to displace the first segment of mandible from the second segment of mandible.

Other aspects and advantages of the present invention can be seen upon review of the figures, the detailed description, and the claims which follow.

BRIEF DESCRIPTION OF THE DRAWINGS

FIG. 4 illustrates a distraction osteogenesis device after activation and removal of a cannula according to the present invention.

FIG. 10 illustrates an alveolar distraction osteogenesis apparatus, including an alveolar distraction device, cannula, torque wrench adapter and torque wrench according to the present invention.

FIGS. 11a–b illustrate an alveolar distraction osteogenesis rod, cannula and torque wrench adapter according to the present invention.

DETAILED DESCRIPTION OF THE INVENTION

I. Distraction Osteogenesis Apparatus

Figure 1:
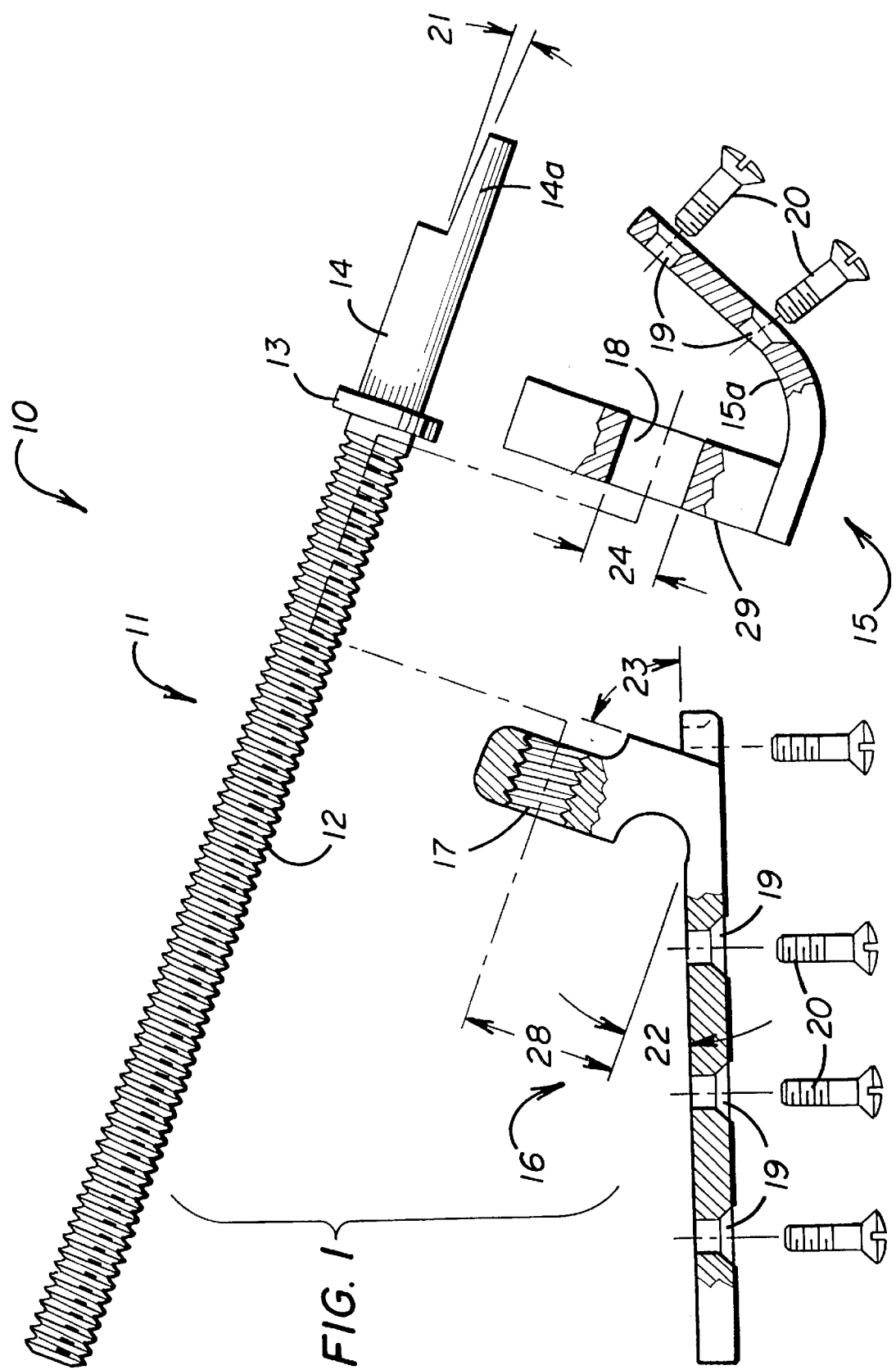
FIG. 1 illustrates a distraction osteogenesis device according to the present invention.

FIG. 1 illustrates distraction osteogenesis device 10 according to the present invention. In a preferred embodiment, distraction osteogenesis device 10 is constructed from titanium. In alternate embodiments, stainless steel or other hardened material may be used. Distraction osteogenesis device 10 is implantable or is inserted under an individual's or animal's soft tissue and/or skin layer. In an embodiment, the distraction osteogenesis device is a LeFort III distractor for the zygoma.

Distraction osteogenesis device 10 includes a rod 11, zygoma posterior plate 16 and zygoma anterior plate 15. Rod 11 includes a threaded portion 12, base 13 and activation end 14. In an embodiment, threaded portion 12 has a diameter of approximately 2.5 mm and a pitch of 0.45 mm per revolution and base 13 has a diameter of approximately 0.1875 inches. In an embodiment, the diameter of activation end 14 is approximately 0.0932 inches. Activation end 14 is used in activating distraction osteogenesis device 10. Bone segments affixed to osteogenesis device 10 are separated responsive to a force which creates a pressure between the bone segments. Activation end 14 includes a tapered bayonet portion 14a having an angle 21 from normal. In an embodiment, angle 21 is approximately 3°.

Figure 2:
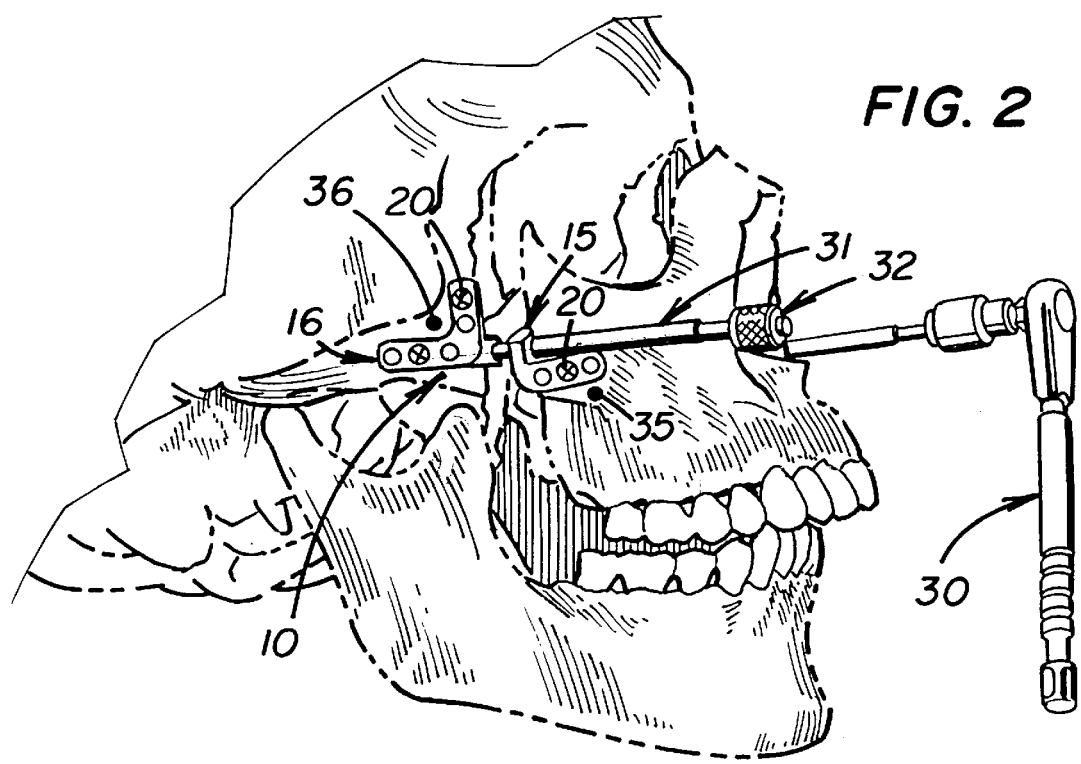
FIG. 2 illustrates a distraction osteogenesis apparatus, including an inserted distraction osteogenesis device, a cannula, a torque wrench adapter and torque wrench according to the present invention.
Figure 3:
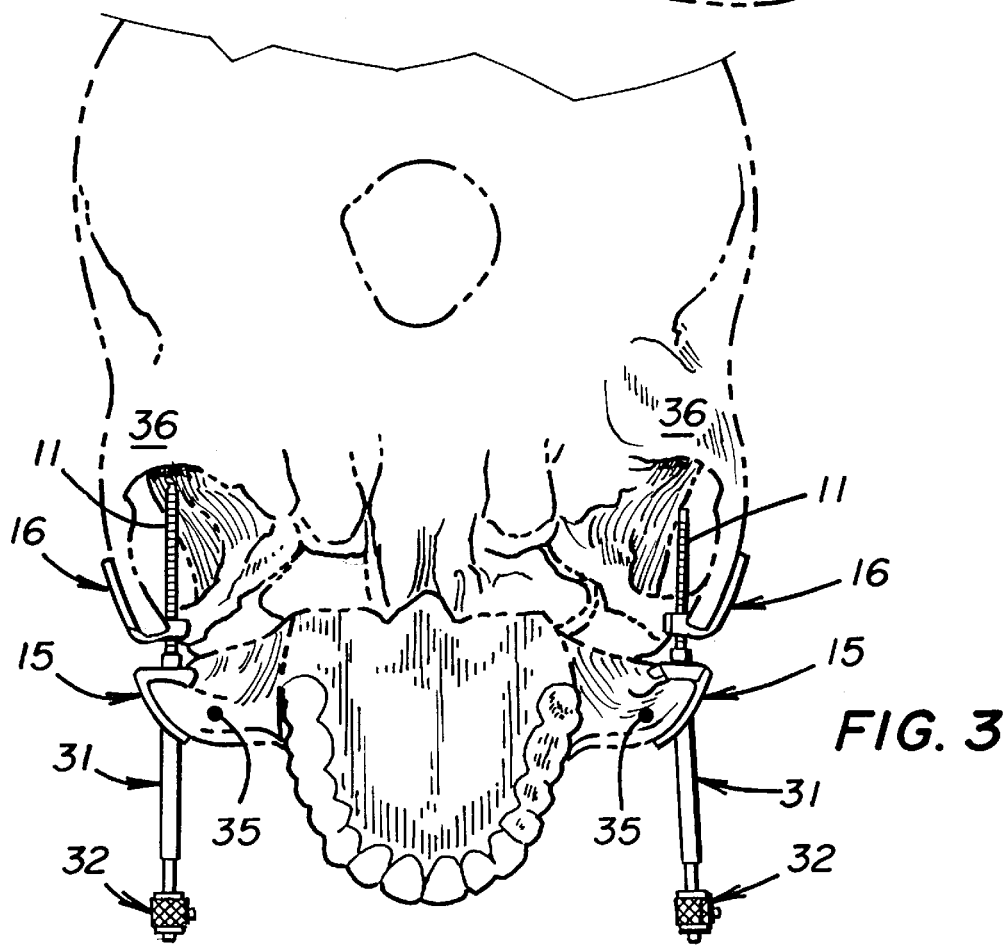
FIG. 3 illustrates a bottom view of a distraction osteogenesis device having self-retaining plates, a cannula and torque wrench adapter according to the present invention.

Zygoma anterior plate 15 has a plurality of openings. Opening 18 has a diameter 24. In an embodiment, diameter 24 is approximately 0.094 inches. Opening 24 is used to position activation end 14 of rod 10. Openings 19 are used for inserting screws 20 which affixes the zygoma anterior plate 15 to the zygoma, as illustrated in FIGS. 2–4. While two openings 19 are illustrated, other embodiments may include a greater or lesser number of openings for fixing the zygoma anterior plate 15, depending upon the positioning of the zygoma anterior plate 15 and the amount of zygoma available. As described in detail below, the zygoma anterior plate 15 is formed in such a way that during activation, a substantial amount of pressure is exerted against, or transferred through, the zygoma anterior plate 15 and not transferred through screws 20. Specifically, the activation force is transferred from rod base 13 against platform 29. Screws 20 are used primarily for fastening the zygoma anterior plate 15 and do not transfer a substantial amount of force during activation. In an embodiment, screws 20 are available from Pfizer Pharmaceuticals, Inc., located at Valley Lab, Inc., P.O. Box 9015, 5920 Longbow Drive, Boulder, Colo. 80301-9015. In an embodiment, screws 20 have a diameter of between approximately 1.5 mm and 2.0 mm. In an embodiment, the diameters of screws 20 are sized such that they are slightly larger than openings 19 in order to fasten plates 15 and 16 by self-threading the openings 19. In another embodiment, the diameters of screws 20 are sized such that there is slight movement between plates and bone.

Zygoma anterior plate 15 is formed in order to be used on a majority of individuals, regardless of size or age.

Similarly, the zygoma posterior plate 16 has a plurality of openings 19. Threaded opening 17 is used to insert threaded portion 12 of rod 10. Openings 19 are used to insert screws 20 for positioning the zygoma posterior plate 16. The zygoma posterior plate 16 is formed in such a way that a substantial portion of the force during activation is transferred through the plate and not the screws 20. Screws 20 are used for fastening the zygoma posterior plate 16, as illustrated in FIGS. 2–4. As above, the diameter of screws 20 is selected in order to self-thread openings 19 or to allow slight movements between plate and bone. The threaded portion of opening 17 is 2.5 mm diameter at a 0.45 mm pitch.

Zygoma posterior plate 16 and zygoma anterior plate 15 is formed in order to be used for most individuals, regardless of age or size. In particular, it was discovered during multiple clinical evaluations that using a distraction osteogenesis device 10 having a certain size and configuration enables a vast majority of individuals to use the distraction osteogenesis device. Specifically, angle 23 was found to be between approximately 65° to 75° and angle 22 to be between approximately 15° and 25°. In a preferred embodiment, angle 22 is approximately 20°. The distance 28 was found to be between 0.1 and 0.3 inches. In the preferred embodiment, distance 28 is 0.2 inches.

FIGS. 2–4 illustrate an inserted and activated distraction osteogenesis device 10. As can be seen from FIG. 2, zygoma anterior plate 15 is positioned by screw 20 to zygoma segment 35 and zygoma posterior plate 16 is positioned to zygoma segment 36 by screw 20. Activation, or separating bone segments 36 and 35, is accomplished by cannula 31, adapter 32 and torque wrench 30. Torque wrench 30, adapter 32 and cannula 31 are also illustrated in FIG. 10. Adapter 32 includes a rod 32a having a tapered bayonet end 32b for fitting rod activation end 14a. FIG. 10 illustrates a cannula length considerably shorter than the one illustrated in FIGS. 2–4. Cannula 31 is first positioned over rod 11, in particular activation end 14. Adapter 32 is then used to couple rod 11 by inserting rod 32a into cannula 31. A hammer is then used to lodge the tapered end 32b of adapter 32 into activation end 14 of rod 11. Torque wrench 30 is then coupled to adapter interface 32c. In an embodiment, the torque wrench 30 may be available from Interpore International, 181 Technology Drive, Irvine, Calif. 92618.

A predetermined torque setting corresponding to a distraction pressure in then set on torque wrench 30. Torque wrench 30 is then rotated in order to create a force which separates plates 16 and 15 and thus bone segments 36 and 35. The torque wrench 30 setting corresponds to a pressure exerted by distraction osteogenesis device 10. The relationship between a torque wrench 30 setting and exerted distraction osteogenesis device 10 pressure is determined before inserting device 10. For example, it was discovered during clinical evaluations that a 14 Newton cm and 18 Newton cm torque wrench setting corresponds to 7 kg and 9 kg of pressure exerted by distraction osteogenesis device 10. The amount of torque applied is based upon the maximum pressure the bone segments can withstand without breaking. This is observed after insertion and before closing. Before the soft tissue or skin is sutured, distraction osteogenesis device 10 is activated until the bone segment appears to bend. This maximum torque setting is then used to maintain a maximum pressure between the bone segments. Throughout the distraction process, this maximum pressure is maintained rather than using conventional activation rates. This maximum pressure thus enables optimized bone growth.

FIG. 3 illustrates a bottom view of distraction osteogenesis device 10 coupled to cannula 31 and adapter 32 for both the left and right side zygoma.

FIG. 4 illustrates an activated, or distracted, distraction osteogenesis device 10 with the cannula 31 and adapter 32 removed. As can be seen, distraction osteogenesis device 10 may be submerged or implanted under an individual's tissue or skin layers. In particular, plate 16, plate 15 and threaded portion 12 of rod 11 may be submerged under an individual's skin. Further, it should be observed that the screws 20 are not used to transfer a substantial amount of the force from torque wrench 30 during activation. Screws 20 are used to position plates 16 and 15 and are positioned substantially perpendicular to the force transferred along rod 11. The plates 16 and 15 are selfretaining in the sense that a substantial amount of the force is transferred through the plates, rather than the fixation points or screws. Thus, distraction osteogenesis device 10 is less likely to break away from bone. Further, more force may also be applied because the screws are not transferring a substantial amount of force.

Figure 5A:
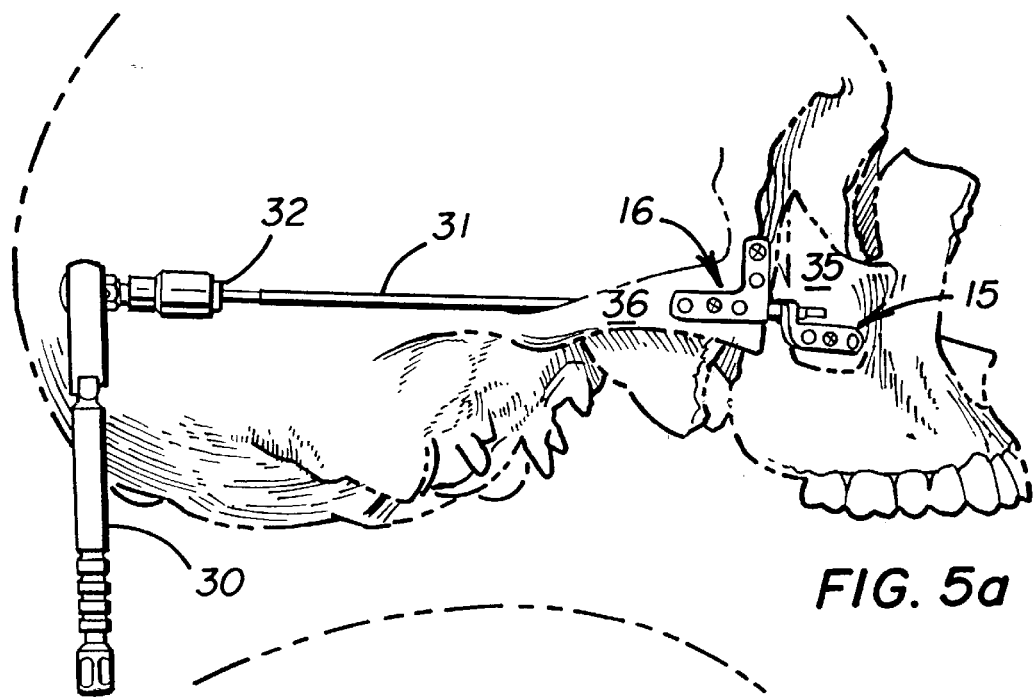
FIGS. 5a–c illustrate a distraction osteogenesis apparatus having a posterior cranial activation according to the present invention.
Figure 5B:
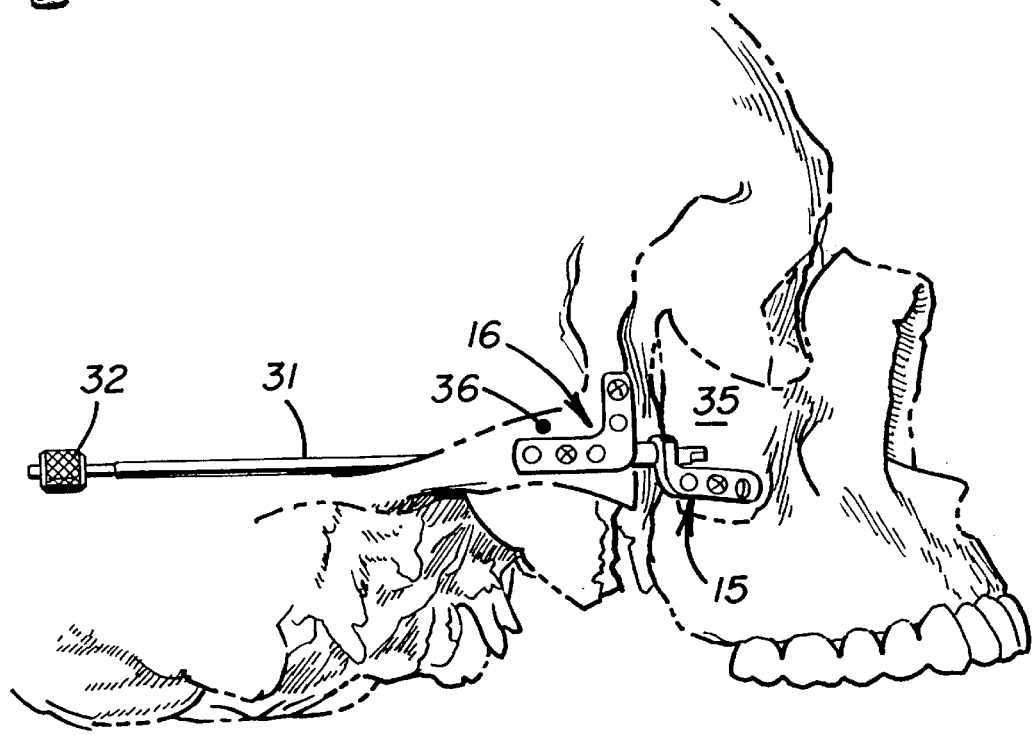
Figure 5C:
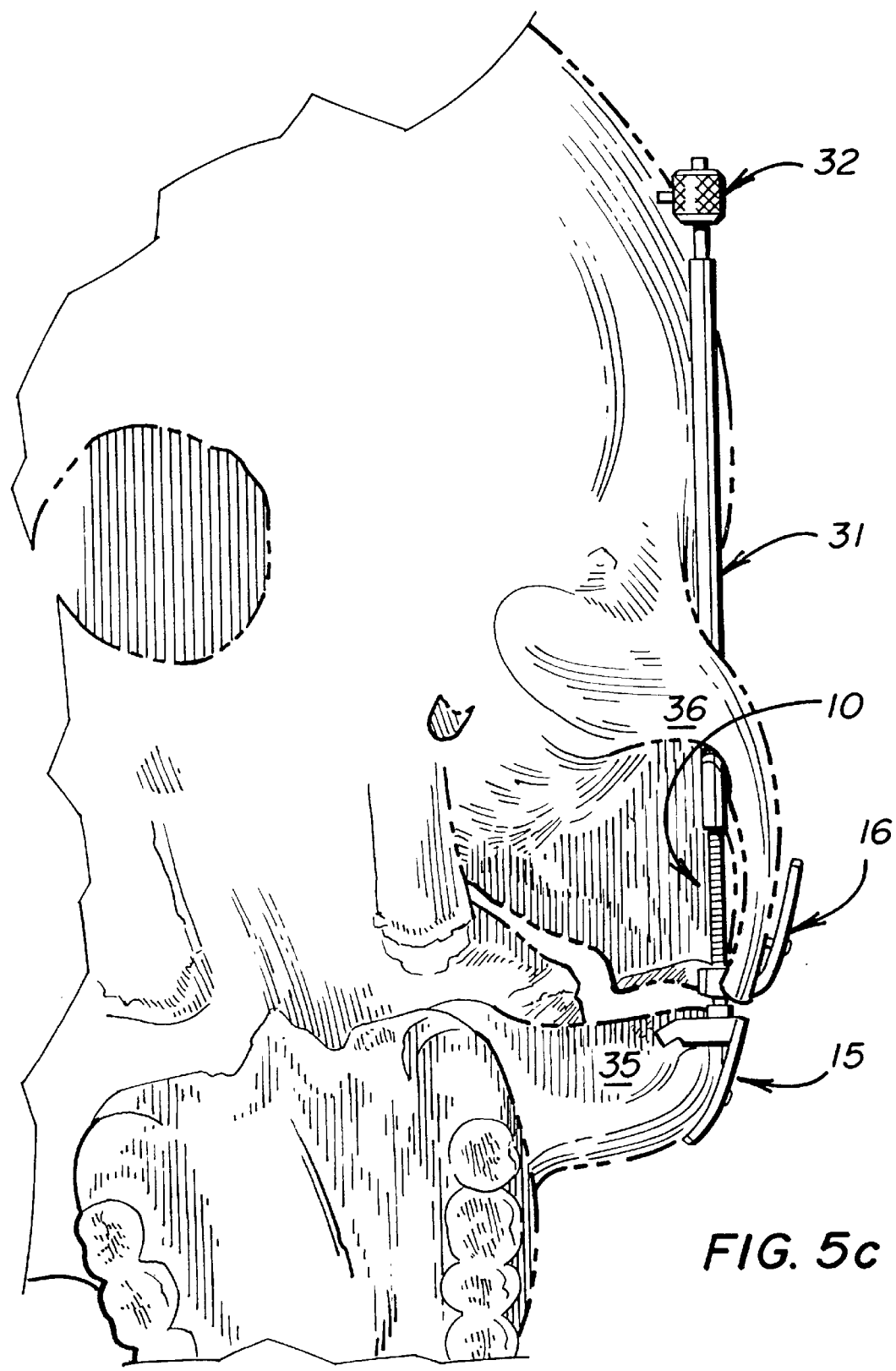

FIGS. 5a–c illustrate a method for inserting zygomatic distraction osteogenesis device 10 in a posterior procedure. Rather than activating distraction osteogenesis device 10 through an opening in the face, the zygomatic distraction device 10 may be activated posterior to, or from the back of, the cranium. FIG. 5a illustrates plate 16 fixed to zygoma segment 36 and plate 15 fixed to zygoma segment 35. In this embodiment, rod 10 would have a similar tapered end 14 at the end of threaded portion 12 for activation. The posteriorly directed activating rod emerges from the surgical incision without requiring a separate skin penetration. FIG. 5a illustrates the cannula 31, torque wrench adapter 32 and torque wrench 30. FIGS. 5b and 5c illustrate zygomatic distraction osteogenesis device 10 without torque wrench 30 and from a bottom view, respectively. This embodiment offers the advantage of not creating facial scars.

Figure 6:
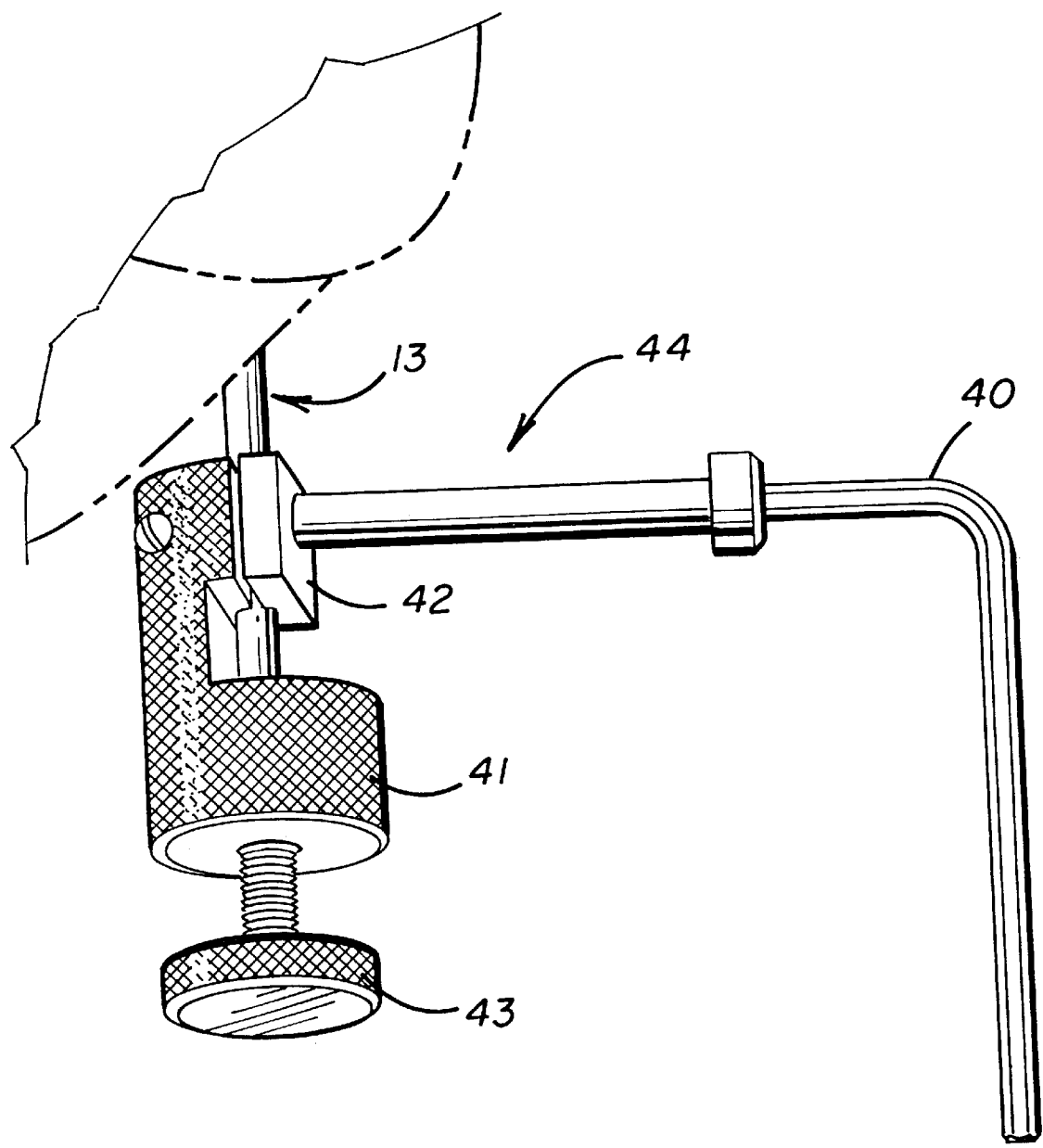
FIG. 6 illustrates a cannula removal device according to the present invention.

FIG. 6 illustrates a cannula and rod removal device 44, according to the present invention. Cannula and rod removal device 44, along with allen wrench 40, is used to remove a cannula 31 and activation rod 32a after activation. Torque wrench interface adapter 32c, as illustrated in FIGS. 2, 3 and 10, is removed before using the cannula and rod removal device 44. Torque wrench adapter interface 32c is coupled to activation rod 32a by a set screw which may be loosened to remove adapter interface 32c. Cannula 31 is secured by clamp 42 by rotating allen wrench 40. After the cannula 31 is secured, the cannula can be removed by rotating knob 43 and holding cylindrical portion 41, forcing a piston against activation rod 32a in cannula 31. The cannula 31 and rod 32a are then dislodged and may be removed.

Figure 7:
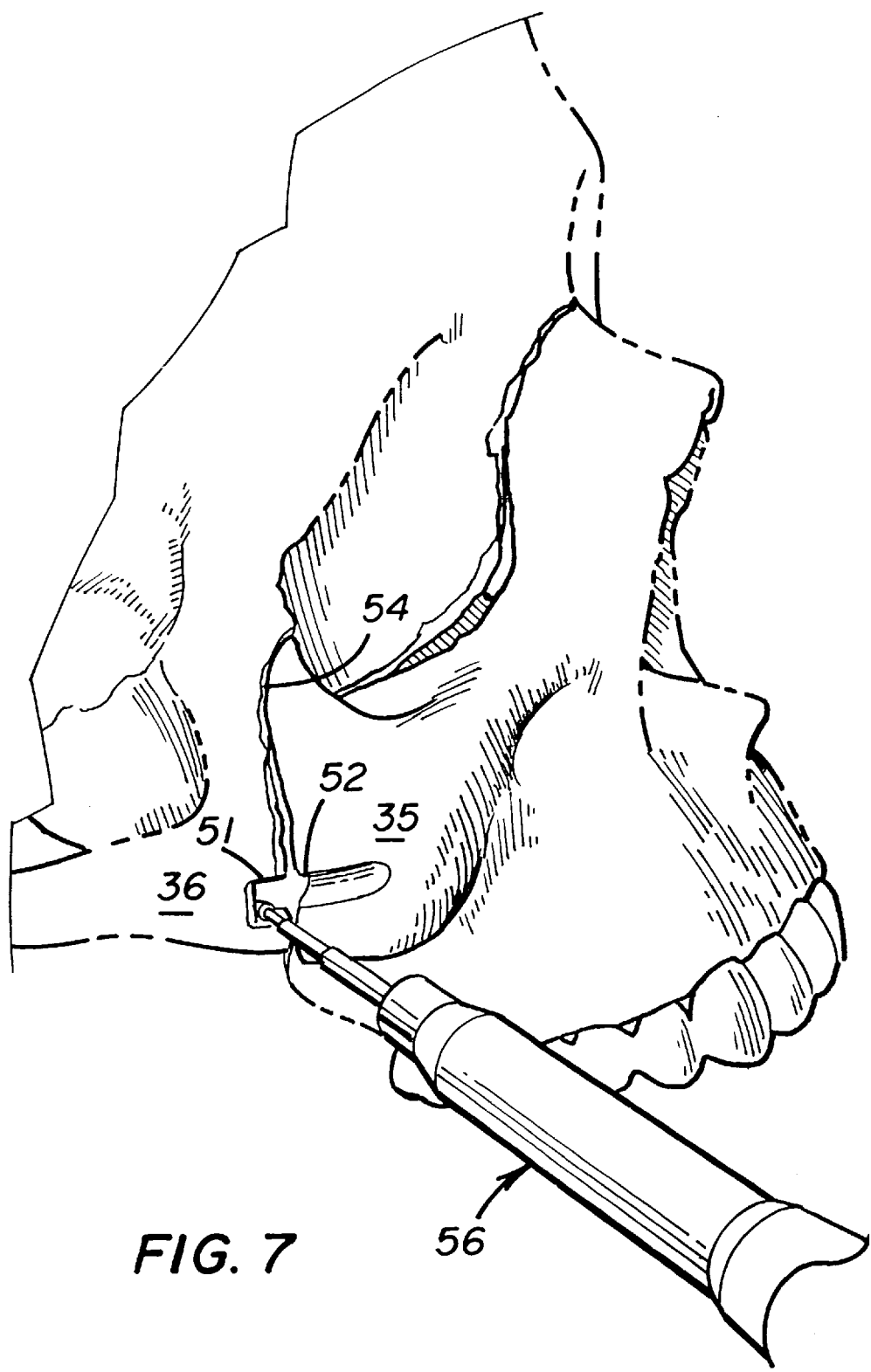
FIGS. 7–9 illustrate the steps for inserting a distraction osteogenesis device according to the present invention.
Figure 8:
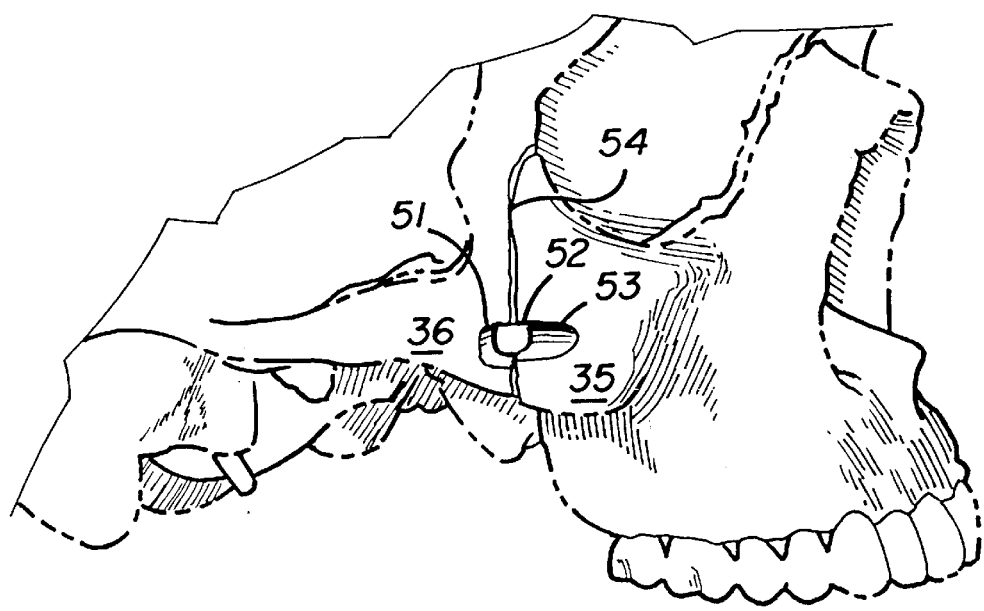
Figure 9:
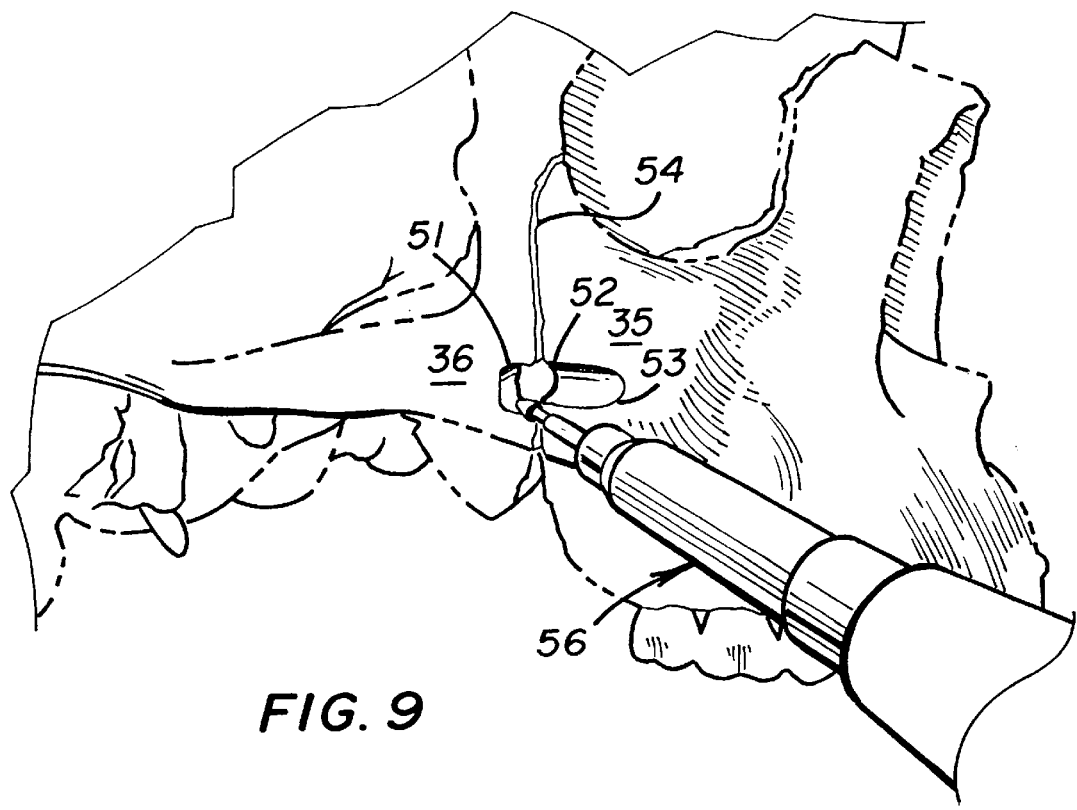

II. Distraction Osteogenesis Device Insertion and Activation Method FIGS. 7–9 illustrate preparing bone segments, for example the zygoma bone, for inserting distraction osteogenesis device 10 according to the present invention. FIGS. 2–4 illustrate activating the inserted distraction osteogenesis device 10, while FIG. 6 illustrates removing a cannula 31 and rod 32a.

In an embodiment, a computed tomography scan of the area for distraction osteogenesis may be obtained. Distraction osteogenesis device 10 may then be manufactured using the information from computed tomography. For example, the length of rod 11 may be determined from this imaging information. Moreover, the amount of bone available and/or number of screws used to affix the distraction osteogenesis device, may be estimated based upon the image information. In the preferred embodiment, a customized distraction osteogenesis device is not used and distraction osteogenesis device 10 having the above-described configuration and size suitable for a majority of individuals is used.

An osteotomy is then performed to create two bone segments 35 and 36 which will be distracted in order to form new bone. FIG. 7 illustrates creating an incision 54 in the zygoma. Indent 51 and 52 are then formed in bone segment 36 and bone segment 35, respectively, by drill 56. As can be seen, notch 51 is slightly larger than notch 52.

FIG. 8 illustrates forming a groove 53 for the curved portion 15a of the zygoma anterior plate 15. FIG. 9 illustrates drill 56 forming notch 51.

A zygoma posterior plate 16 is then inserted into indent 51 and fastened to zygoma 36 by screws 20, as illustrated in FIG. 2. The number of screws used depends upon the bone available. Zygoma anterior plate 15 is then inserted into indent 52 and groove 53 and fixed by screws 20. In the preferred embodiment, anterior plate 15 is inserted by wedging platform 29 into incision 54 or between notches 51 and 52. Anterior plate 15 then is rotated to fit against zygoma bone 35. Likewise, the number of screws used depends upon the amount of bone available. Rod 11 then may be inserted through openings 17 and 18. In particular, the thread portion of rod 11 is screwed into opening 17, while rod base 13 is positioned against platform 29 of plate 15, allowing for tapered end 14 to be inserted through opening 18. A cannula 31 and adapter 32 having activation rod 32a is then positioned, as illustrated in FIG. 2. The cannula may be positioned over tapered end 14 by way of a thin positioning rod. Torque wrench 30 is then screwed to adapter 32. Torque wrench 30 is then rotated to a predetermined torque setting corresponding to a maximum pressure. Rather than using a constant activation rate, the distraction osteogenesis device exerts a maximum pressure between zygoma segments 35 and 36. The pressure is monitored throughout the day and additional torque is applied in order to maintain a maximum pressure. This maximum pressure on the zygoma optimizes bone growth, requiring the shortest activation period possible. Using conventional activation rates allows for the pressure to decrease from a maximum range. Maintaining a maximum pressure range on the bone segments 35 and 36 allows for maximum bone growth and requires the minimal activation period possible.

Cannula 31 and adapter 32 then may be removed, as described above and illustrated in FIG. 6.

Thus, distraction osteogenesis device 10 is submerged beneath soft tissue and/or a layer of skin. The submerged distraction osteogenesis device reduces the likelihood of infection, as well as trauma, which may be caused by a fall or improper activation of the distraction device. Further, the submergible distraction osteogenesis device is less likely to leave scars and is more cosmetically appealing than external distraction osteogenesis devices. Using an activation rate based on an individual's ability to generate bone allows for increased bone growth. During clinical studies, 20 mm of bone growth was obtained in two days, as opposed to using conventional activation rates requiring up to 25 days.

III. Alveolar Distraction Osteogenesis Apparatus

FIG. 10 illustrates alveolar distraction osteogenesis apparatus 68. The alveolar distraction osteogenesis apparatus 68 is used to form bone in the alveolus which may be missing due to an accident or birth abnormality. Often, alveolus must be formed in order for dental implants to be used. Similar to the distraction osteogenesis apparatus illustrated in FIGS. 1 and 2, the alveolar distraction osteogenesis apparatus 68 includes a torque wrench 30, adapter 32 and cannula 31.

The alveolar distraction osteogenesis apparatus 68 also includes an alveolar distraction osteogenesis device 69. The alveolar distraction osteogenesis device 69 includes a rod 60 having base 61, activation end 62 and end 60a. The alveolar distraction osteogenesis device 69 also includes a transport bone segment plate 63 and stabilizing plate 64. Plates 63 and 64 may be secured by screws 66 and 65, respectively.

FIGS. 11a–b illustrate two embodiments of an alveolar distraction osteogenesis device 69 shown in FIG. 10. FIG. 11a illustrates a nonsubmergible alveolar distraction osteogenesis device, while FIG. 11b illustrates a submergible alveolar distraction osteogenesis device. The nonsubmergible alveolar distraction osteogenesis device in FIG. 11a incldes rod 70, cannula 72 and adapter 73. Rod 70 includes base 71 and end 78. The submergible alveolar distraction osteogenesis device shown in FIG. 11 includes rod 74, cannula 76 and adapter 77. Rod 74 includes base 75 and end 79 The nonsubmergible alveolar distraction osteogenesis device illustrated in FIG. 11a has a rod 70 with a base 71 which may be positioned substantially above soft tissue and/or a skin layer, while base 75 of rod 74 is positioned below soft tissue and/or a skin layer. Finally, the alveolar distraction osteogenesis device illustrated in FIG. 11b has a diameter of approximately 1.6 mm and a pitch of 0.35 mm per revolution, while the alveolar distraction osteogenesis device illustrated in FIG. 11a has a diameter of approximately 2.0 mm and a pitch of 0.4 mm per revolution.

Figure 12B:
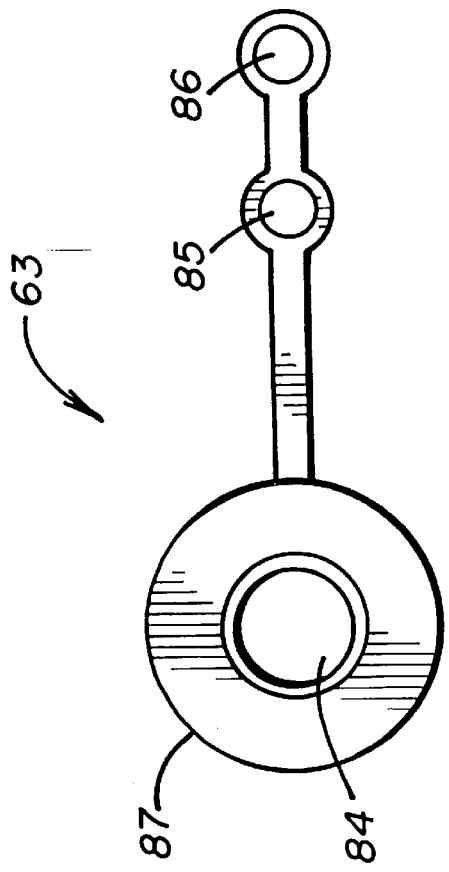
FIGS. 12a–c illustrate alveolar distraction osteogenesis plates according to the present invention.
Figure 12C:
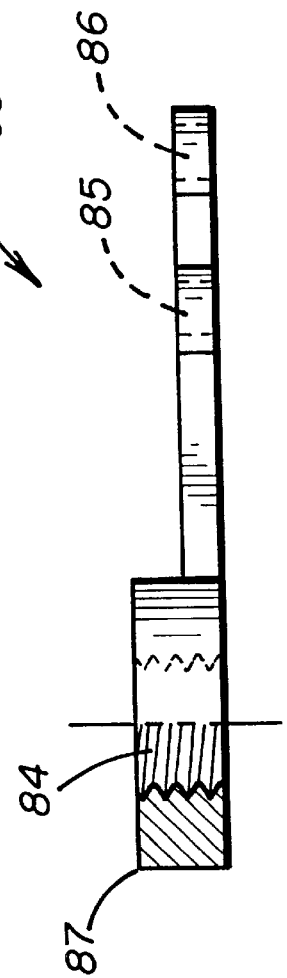
Figure 12A:
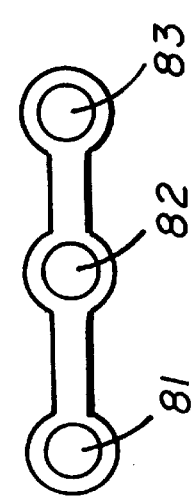

FIGS. 12a–c illustrate the transport bone segment plate 63 and stabilizing plate 64 illustrated in FIG. 10. In an embodiment, stabilizing plate 64 consists of a titanium member having openings 81, 82 and 83. In an embodiment, a greater or lesser amount of openings may be used. Openings 82 and 83 are used to fix plate 64 to bone with inserted screws. Further, embodiments may not require plate 64 if the bone material is sufficiently hard. The titanium member may be bent approximately 90° between openings 81 and 82, as seen in plate 64 of FIG. 10, to fit the alveolus. In an embodiment, opening 83 is an approximately 1 mm opening for positioning a rod, such as rod end 79 shown in FIG. 11b.

In an embodiment, transport bone segment plate 63 also is a titanium member having three openings 84, 85 and 86, as illustrated in FIGS. 12b–c. In an embodiment, a greater or lesser amount of openings may be used. Openings 85 and 86 are used to fix transport bone segment plate 63 to bone with inserted screws. In an embodiment, both plates 64 and 63 are available from Pfizer Pharmaceuticals, Inc., located at Valley Lab, Inc., P.O. Box 9015, 5920 Longbow Drive, Boulder, Colo. 80301-9015. The screws, such as screws 66 and 65, as shown in FIG. 10, are also available from Pfizer Pharmaceuticals, Inc. In an embodiment, the diameter of washer-shaped member 87 surrounding opening 84 is approximately 0.175 inches, while openings at 85 and 86 are approximately 1.0 mm. In an embodiment, the width of the washershaped member 87 is approximately 5 mm. The threaded portion of opening 84 has a diameter of approximately 2 mm and a pitch of 0.4 mm per revolution for rod 70 and approximately 1.6 mm and a pitch of 0.35 mm per revolution for rod 74. Threaded opening 84 is used to position rod 60. As with plate 64, transport bone segment plate 63 may be bent approximately 90° between openings 85 and 84, as seen in transport bone segment plate 63 of FIG. 10, to fit the alveolus.

As with the zygoma distraction described above, the alveolar distraction osteogenesis device may be implanted, and is thus submergible, beneath a layer of soft tissue.

Thus, the alveolar distraction osteogenesis device is less likely to scar and is more cosmetically appealing and comfortable than external distraction osteogenesis devices. A submerged alveolar distraction osteogenesis device is less likely to become infected than external devices. Also, the fixation points, in particular screws, which fix the plates to bone do not transfer a substantial amount of force during activation. The screws are used to fix the plates and are inserted substantially perpendicular to the pressure separating the bone segments. The alveolar distraction osteogenesis device may also be activated using a maximum pressure, rather than at conventional constant activation rates, as described above.

IV. Alveolar Distraction Osteogenesis Device Inserting and Activating Method

Figure 13A:
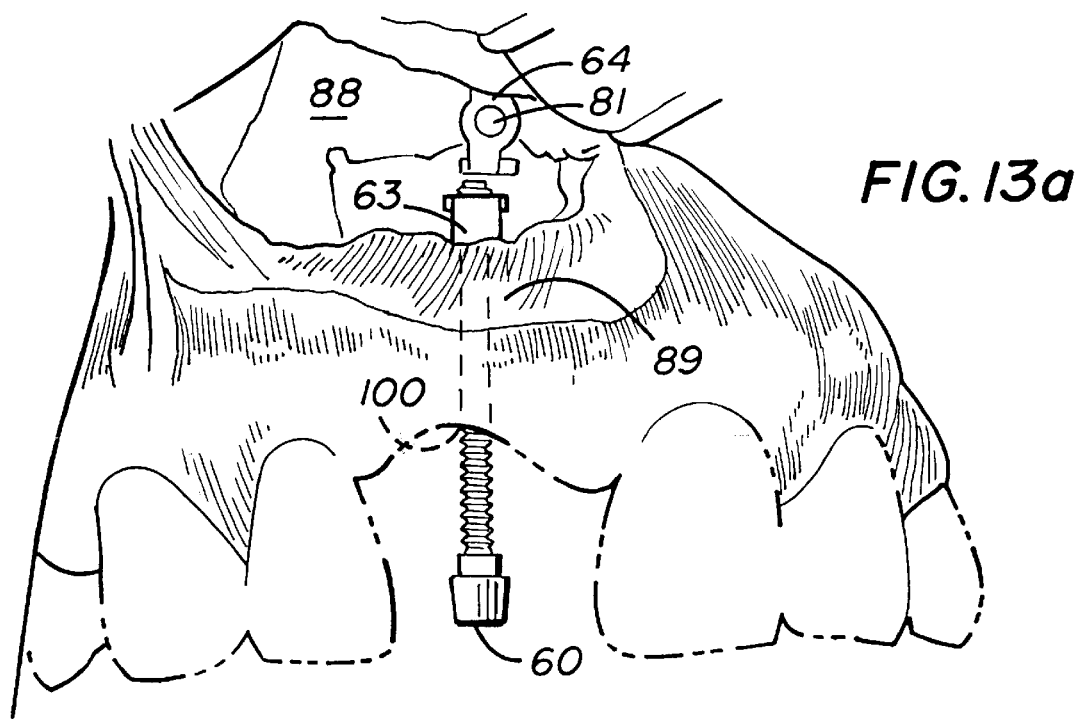
FIGS. 13a–b illustrate the steps of inserting an alveolar distraction osteogenesis device according to the present invention.
Figure 13B:
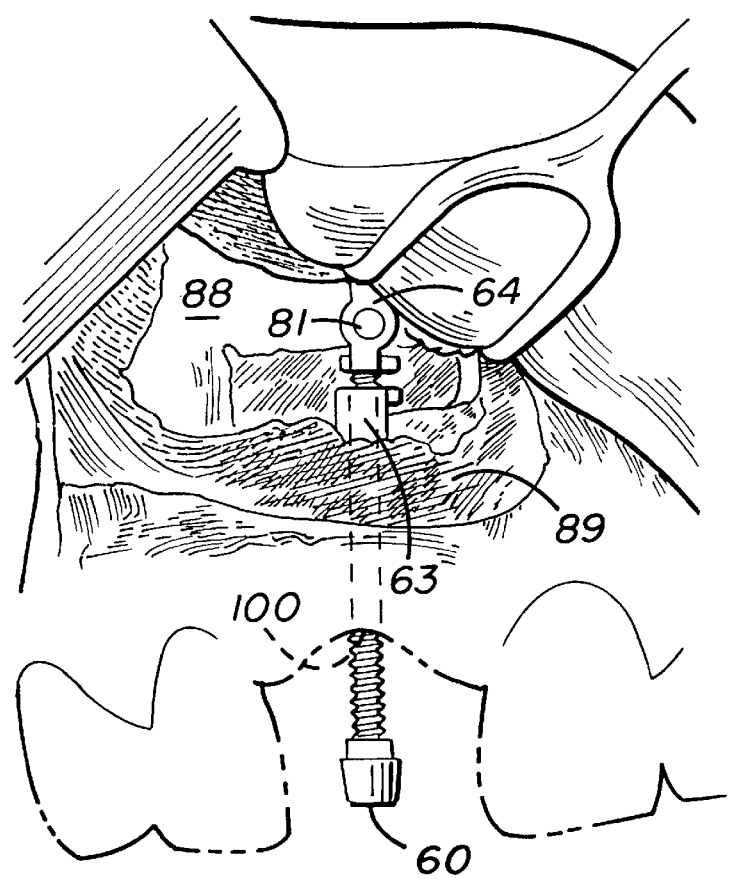

FIGS. 13a–b illustrate a surgical view of an osteotomy and an inserted alveolar distraction osteogenesis device according to the present invention. Specifically, FIGS. 13a–b illustrate a rod 60 inserted into stabilizing plate 64 and transport bone segment plate 63.

After determining the size of rod 60, an osteotomy is performed on the alveolus to form upper alveolus segment 88 and lower alveolus segment 89. An opening 100 is then drilled into the lower alveolus segment 89. In an embodiment, an approximately 2 mm wide opening is formed. Stabilizing plate 64 is then positioned on the upper alveolus segment 88, while bone transport segment plate 63 is positioned on the lower alveolus segment. Bone screws then may be positioned through openings 81, 82, 85 and 86 to fix the plates 63 and 64 to respective alveolus segments. FIGS. 13a–b illustrate a plate 64 without a screw in opening 81. Rod 60 is then inserted into opening 100 through lower alveolus segment 89 and through opening 84 of plate 63. Rod end 60a is then positioned in opening 83 of plate 64.

Figure 14A:
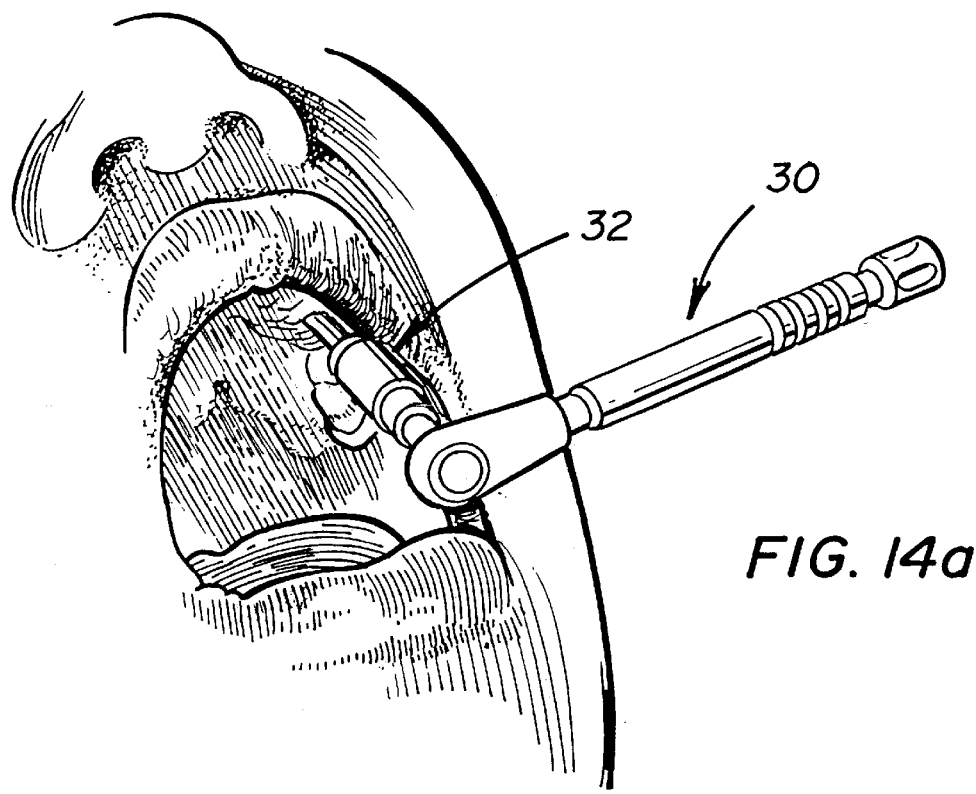
FIG. 14a illustrates activating an inserted alveolar distraction osteogenesis device according to the present invention.

As described in regard to the zygomatic distraction osteogenesis device above, the alveolar distraction osteogenesis device may be activated using a torque wrench 30 and adapter 32, as illustrated in FIG. 14a. As described above, a maximum pressure may be exerted between upper alveolus 88 and lower alveolus 89 by setting the torque wrench to a predetermined setting. Thus, a relatively constant maximum pressure may be obtained, ensuring optimal bone growth.

Figure 14B:
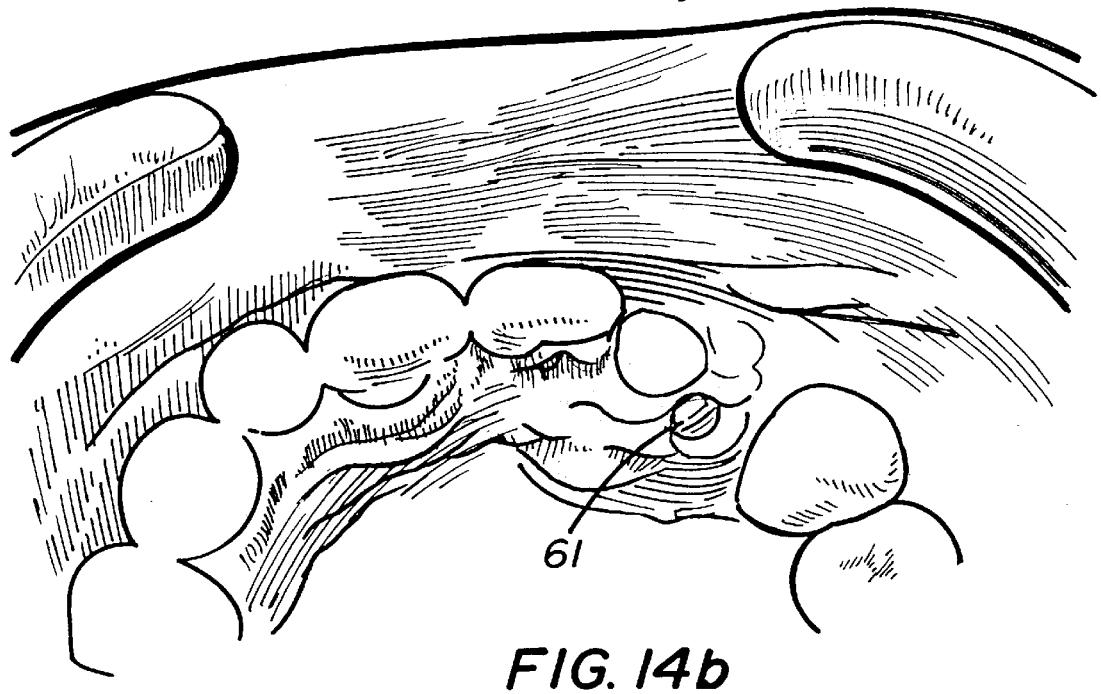
FIG. 14b illustrates an inserted activated alveolar distraction osteogenesis device according to the present invention.

FIG. 14b illustrates a submerged alveolar distraction osteogenesis device in which only base 61 of rod 60 is visible. In an embodiment, base 61 may be used to position a temporary dental prosthesis. Thus, the alveolar distraction device is implanted and has a more cosmetically appealing appearance.

V. Mandibular Distraction Osteogenesis Device

Figure 15:
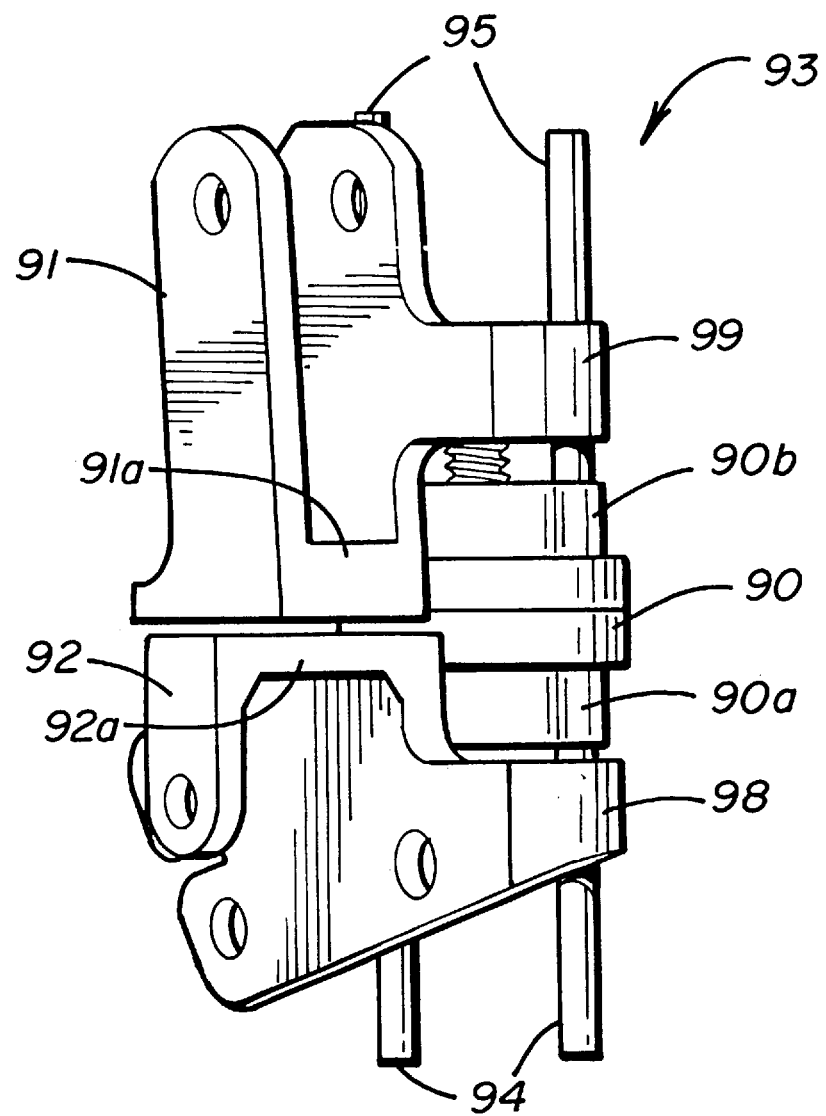
FIG. 15 illustrates a mandibular distraction osteogenesis device according to the present invention.
Figure 16A:
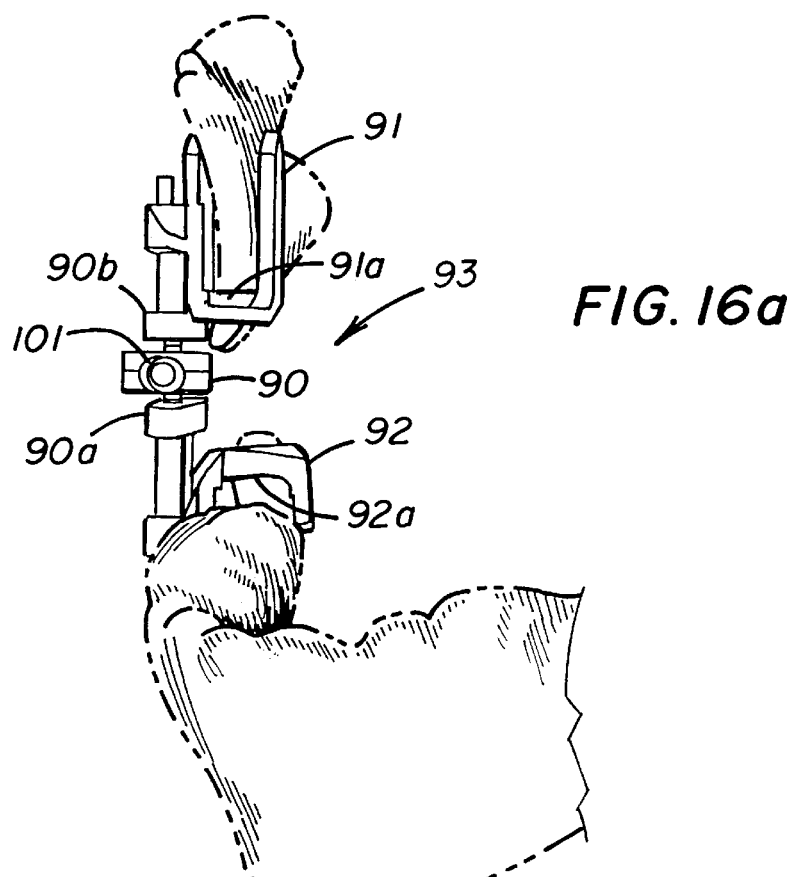
FIG. 16a illustrates an inserted mandibular distraction osteogenesis device in an activated position according to the present invention.
Figure 16B:
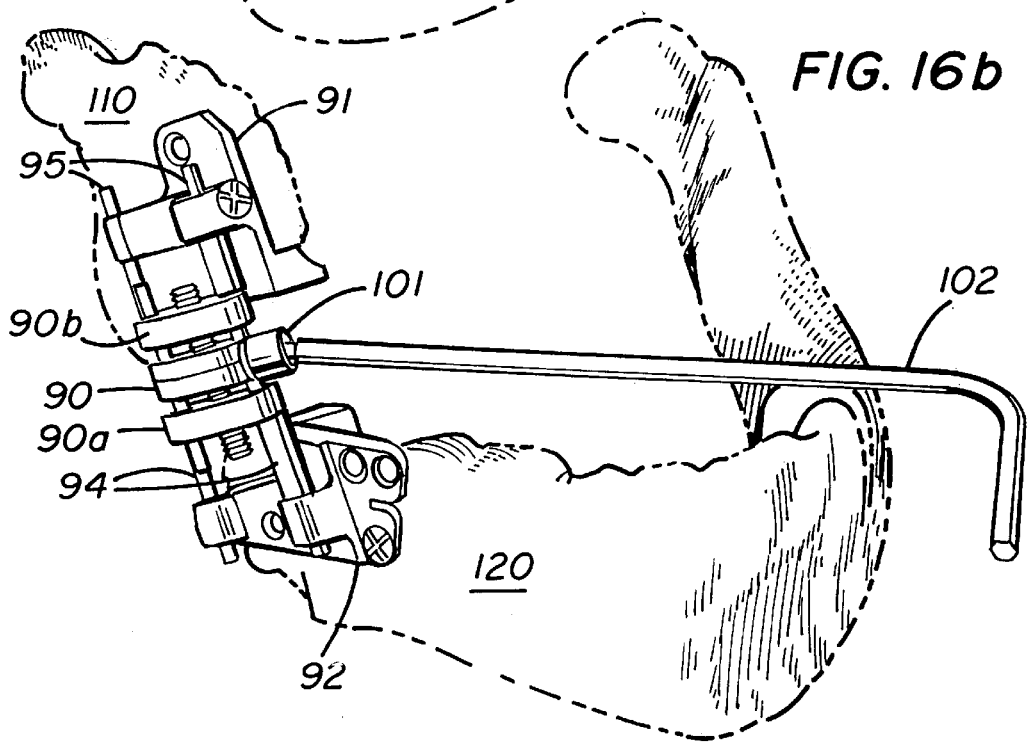
FIG. 16b illustrates an inserted mandibular distraction osteogenesis device in an activated position and an allen wrench according to the present invention.
Figure 17B:
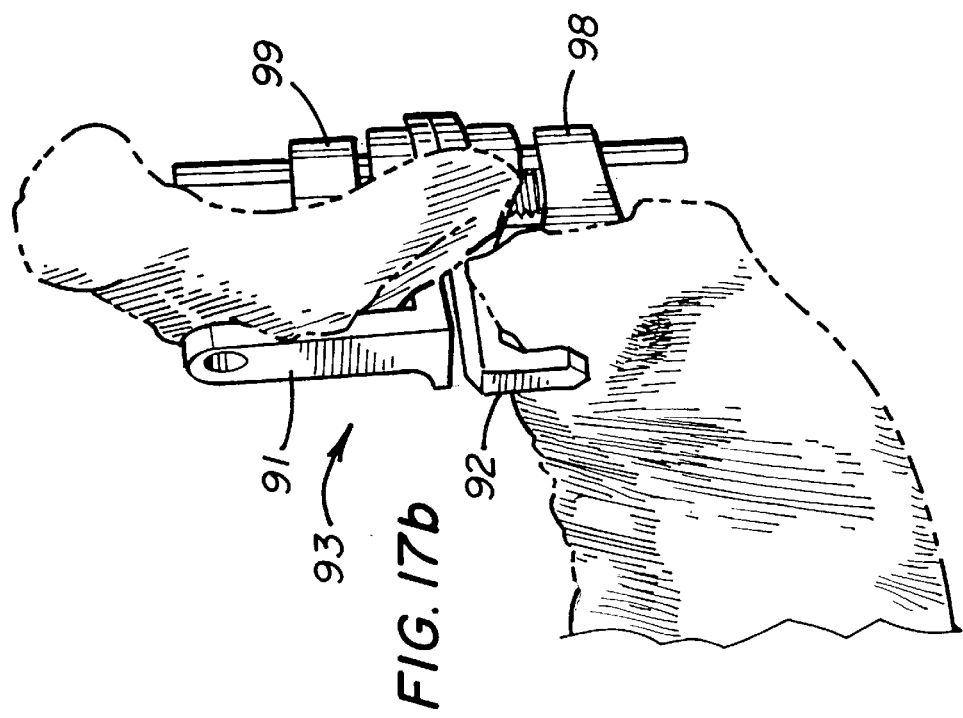
FIG. 17b illustrates a medial view of a mandibular distraction osteogenesis device having self-retaining flanges according to the present invention.
Figure 17A:
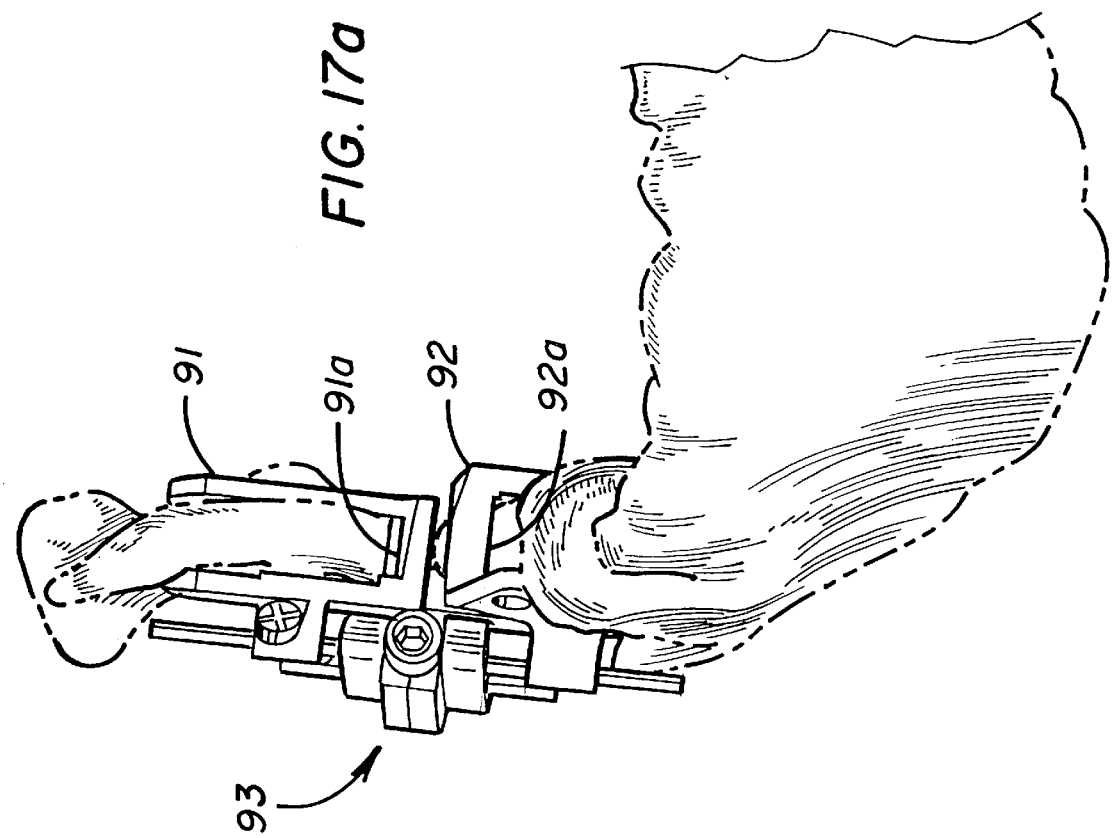
FIG. 17a illustrates an inserted mandibular distraction osteogenesis device in a non-activated position according to the present invention.

FIG. 15 illustrates a mandibular distraction osteogenesis device 93 according to the present invention. Mandibular distraction osteogenesis device 93 includes a palate expander 90, along with self-retaining plates 91 and 92, as seen in FIGS. 15–18. In an embodiment, distraction osteogenesis device 93 is constructed from stainless steel. In an embodiment, the palate expander 90 is a Lariats palate expander available from Easy Access Orthodontics, located at 2701 LaPaz Road, #236, Mission Viejo, Calif. 92691. The palate expander 90 includes two extending components 90a and 90b which extend responsive to applying a torque at allen wrench opening 101 in palate expander 90. FIGS. 16a–b illustrate a mandibular extraction device 93 in an activated position. Allen wrench 102 is inserted into allen wrench opening 101. A torque then expands extracting components 90a and 90b. Extending components 90a and 90b are coupled to respective pairs of rods 94 and 95, as seen in FIG. 16b. The pairs of rods 94 and 95 are then used to couple to self-retaining plates 92 and 91. Self-retaining plates 91 and 92 are formed in a U-shaped manner having a plurality of openings, as seen in FIGS. 17a–b. Self-retaining plates 91 and 92 have flanges for gripping bone segments.

Figure 18:
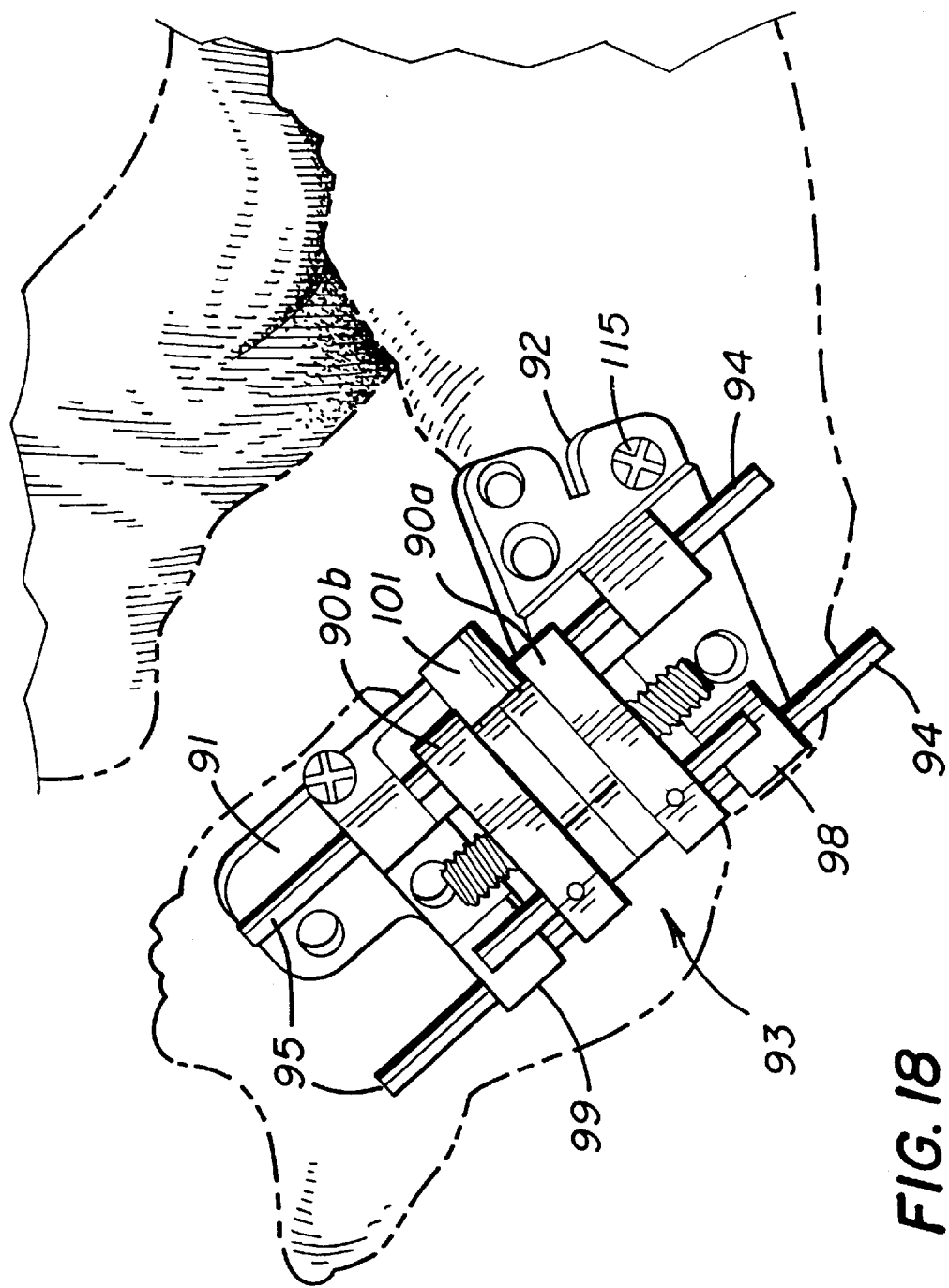
FIG. 18 illustrates an inserted mandibular distraction osteogenesis device in a non-activated position according to the present invention.

Openings in plates 91 and 92 are also used to fasten the self-retaining plates 91 and 92 to mandible bone segments by screws. For example, screw 115 is used to fasten self-retaining plate 92, as shown in FIG. 18.

As with the distraction osteogenesis devices described above, submergible mandibular distraction osteogenesis device 93 has plates which transfer a substantial amount of pressure between bone segments rather than through fixation points. As extracting components 90b and 90a move responsive to a torque being applied, force transfers through self-retaining plates 91 and 92 and not through the screws used to fasten plates 91 and 92 to the mandible. Specifically, pressure is exerted at platforms 91a and 92a of plates 91 and 92, respectively, as shown in FIGS. 16a and 17a.

VI. Mandibular Distraction Osteogenesis Device Insertion and Activation Method

As described above with respect to the other distraction osteogenesis devices, a computed tomography scan of a mandible may be obtained before insertion and activation in order to determine the amount of bone available. An osteotomy is then performed in order to create mandibular bone segment 110 and mandibular bone segment 120, as seen in FIG. 16b. Self-retaining plates 91 and 92 are then positioned on pairs of rods 94 and 95 by inserting the rods through openings in protruding edges 98 and 99, respectively, of plates 92 and 91, as seen in FIGS. 17b and 18. Mandibular distraction osteogenesis device 93, including palate expander 90 which is coupled to selfretaining plates 91 and 92, is then inserted between mandibular bone segments 110 and 120. Bone screws can then be inserted into the openings in self-retaining plates 91 and 92.

Mandibular distraction osteogenesis device 93 then may be activated by inserting an allen wrench 102 into an allen wrench opening 101 in palate expander 90, as seen in FIG. 16b. One full clockwise rotation of the activation allen wrench opening 101 equals 0.2 mm of expansion. A pressure can then be produced, forcing extending components 90a and 90b from palate expander 90, thus displacing mandibular bone segment 110 from mandibular bone segment 120. The allen wrench opening 101 of palate expander 90 may be accessed through the mouth or an opening on the face.

As described above, the submergible mandibular distraction osteogenesis device 93 may be activated using a maximum pressure rate, rather than the conventional activation rate. Similarly, mandibular distraction osteogenesis device 93 offers the advantages described above in regard to the zygomatic and alveolar distraction osteogenesis devices The foregoing description of the preferred embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An apparatus for distracting a first bone segment from a second bone segment, comprising:
   (a) an implantable first plate for coupling the first bone segment;
   (b) an implantable second plate for coupling the second bone segment;
   (c) submergible means, coupled to the first plate and the second plate, for positioning the first plate a distance from the second plate responsive to a force;
   (d) activating means, coupled to the submergible means, for transferring a force; wherein the activating means includes:
   (e) a cannula;
   (f) it a torque wrench adapter; and,
   (g) a torque wrench.

2. The apparatus of claim 1, further comprising means for removing the activating means.

3. A submergible device for distracting a first segment of the alveolus from a second segment of the alveolus to allow for bone generation, comprising:
   (a) rod having a threaded portion, an end, and an activation end;
   (b) a first member for coupling to the first segment of the alveolus. having an opening for inserting the rod end;
   (c) a second member for coupling to the second segment of the alveolus having an opening for positioning the threaded portion of the rod, wherein the rod transfers a first force against the second member, creating a distance between the first and second alveolus segments; wherein a device for transferring the first force includes;
   (d) a cannula for inserting over the rod activation end;
   (e) a torque wrench adapter having an activation end for inserting into the cannula; and,
   (f) a torque wrench for transferring the first force to the second member.

4. A device for removing the cannula of claim 3, comprising:
   (g) a clamp for tightening the cannula; and,
   (h) a moveable piston for exerting a second force against the torque wrench adapter activation end.

5. A method for forming alveolus, comprising the steps of:
   (a) cutting the alveolus into first and second segments;
   (b) securing a plate to the first segment of the alveolus;
   (c) forming an opening in the second segment of the alveolus;
   (d) securing a transport plate to the second segment of the alveolus;
   (e) inserting a rod into the opening of the second segment of the alveolus and through the transport plate to the first plate; and,
   (f) exerting a force on the rod in order to displace the first segment of the alveolus from the second segment of the alveolus.

* * * * *